(12) United States Patent
Choi et al.

(10) Patent No.: US 12,035,884 B2
(45) Date of Patent: *Jul. 16, 2024

(54) SPINAL NERVE DECOMPRESSION SYSTEMS, DILATION SYSTEMS, AND METHODS OF USING THE SAME

(71) Applicant: VertiFlex, Inc., San Clemente, CA (US)

(72) Inventors: Andy Choi, Irvine, CA (US); Kim Nguyen, Oceanside, CA (US); Martin Leugers, Newark, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/741,258

(22) Filed: May 10, 2022

(65) Prior Publication Data

US 2022/0265258 A1    Aug. 25, 2022

Related U.S. Application Data

(63) Continuation of application No. 16/678,801, filed on Nov. 8, 2019, now Pat. No. 11,357,489, which is a
(Continued)

(51) Int. Cl.
*A61B 17/02* (2006.01)
*A61B 1/00* (2006.01)
(Continued)

(52) U.S. Cl.
CPC ...... *A61B 1/00148* (2022.02); *A61B 1/00087* (2013.01); *A61B 1/00154* (2013.01);
(Continued)

(58) Field of Classification Search
CPC ..... A61B 17/02; A61B 17/0218; A61B 17/34; A61B 17/3423; A61B 17/0293;
(Continued)

(56) References Cited

U.S. PATENT DOCUMENTS 2,248,054 A    7/1941  Becker
2,677,369 A    5/1954  Knowles
(Continued)

FOREIGN PATENT DOCUMENTS

CA    268461 A    2/1927
CN    2794456 Y    7/2006
(Continued)

OTHER PUBLICATIONS

Official Communication for U.S. Appl. No. 15/309,164 mailed Apr. 2, 2019.
(Continued)

*Primary Examiner* — Christopher J Beccia
(74) *Attorney, Agent, or Firm* — Branch Partners PLLC; Bruce E. Black

(57) ABSTRACT

A method for treating spinal nerve compression includes sequential dilation to position an instrument cannula along a patient's spine. Instruments can be delivered through the instrument cannula to remove targeted tissue for a decompression procedure. One of the instruments can be a reamer instrument configured to abrade, cut, or otherwise affect tissue along the patient's spine.

20 Claims, 27 Drawing Sheets

Related U.S. Application Data continuation of application No. 15/309,164, filed as application No. PCT/US2015/029537 on May 6, 2015, now Pat. No. 10,524,772.

(60) Provisional application No. 62/060,965, filed on Oct. 7, 2014, provisional application No. 61/990,030, filed on May 7, 2014.

(51) Int. Cl.

| | | |
|---|---|---|
| *A61B 1/07* | (2006.01) | |
| *A61B 1/313* | (2006.01) | |
| *A61B 1/32* | (2006.01) | |
| *A61B 17/16* | (2006.01) | |
| *A61B 17/34* | (2006.01) | |
| *A61B 90/00* | (2016.01) | |
| *A61B 90/30* | (2016.01) | |
| *A61M 29/00* | (2006.01) | |
| *A61B 17/00* | (2006.01) | |
| *A61B 17/32* | (2006.01) | |

(52) U.S. Cl.
CPC .............. *A61B 1/07* (2013.01); *A61B 1/3135* (2013.01); *A61B 1/32* (2013.01); *A61B 17/0218* (2013.01); *A61B 17/0293* (2013.01); *A61B 17/1671* (2013.01); *A61B 17/3401* (2013.01); *A61B 17/3423* (2013.01); *A61B 90/30* (2016.02); *A61B 90/361* (2016.02); *A61M 29/00* (2013.01); *A61B 2017/00477* (2013.01); *A61B 2017/0256* (2013.01); *A61B 2017/320008* (2013.01); *A61B 17/32002* (2013.01); *A61B 2017/3407* (2013.01); *A61B 2090/062* (2016.02); *A61B 2090/306* (2016.02)

(58) Field of Classification Search
CPC ... A61B 17/32; A61B 17/313; A61B 17/3135; A61B 1/00
See application file for complete search history.

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |

(56) References Cited

U.S. PATENT DOCUMENTS

| | | |
|---|---|---|
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |

(56) References Cited

U.S. PATENT DOCUMENTS

| | | |
|---|---|---|
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 10,524,772 B2* | 1/2020 | Choi ............... A61B 90/30 |
| 2001/0031965 A1 | 10/2001 | Zucherman et al. |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |

(56) References Cited

U.S. PATENT DOCUMENTS

| | | |
|---|---|---|
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1* | 9/2012 | Morgenstern Lopez .................... A61B 5/4893 606/45 |
| 2012/0303039 A1* | 11/2012 | Chin .................. A61B 17/0206 606/191 |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |

(56) References Cited

U.S. PATENT DOCUMENTS

| | | | |
|---|---|---|---|
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |
| 2016/0030092 A1 | 2/2016 | Altarac et al. |
| 2016/0045232 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |
| 2016/0317193 A1 | 11/2016 | Kim |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

Official Communication for U.S. Appl. No. 16/678,801 mailed Dec. 7, 2021.

(56) References Cited

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Decision on Petition in U.S. Appl. No. 60/592,099, filed May 4, 2005.
Fast, Avital et al., "Surgical Treatment of Lumbar Spinal Stenosis in the Elderly," Arch Phys. Med Rehabil., Mar. 1985, pp. 149-151, vol. 66.
International Search Report and Written Opinion; Application No. PCT/US2015/029537; Applicant: Vertiflex, Inc. Mailing Date: Aug. 3, 2015, 14 pages.
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1827.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Swan, Colby, "Preliminary Design and Experimental Studies of a Novel Soft Implant for Correcting Sogittal Plane Instability in the Lumbar Spine," Spine, 1997, 22(16), 1826-1827.
Tredway, Trent L. et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos mild Devices Kit—PRT-00430-C—Instructions for Use (13 pages total); see http://vertosmed.com/docs/mildIFU_PRT-00430-C.pdf., 2012.

* cited by examiner

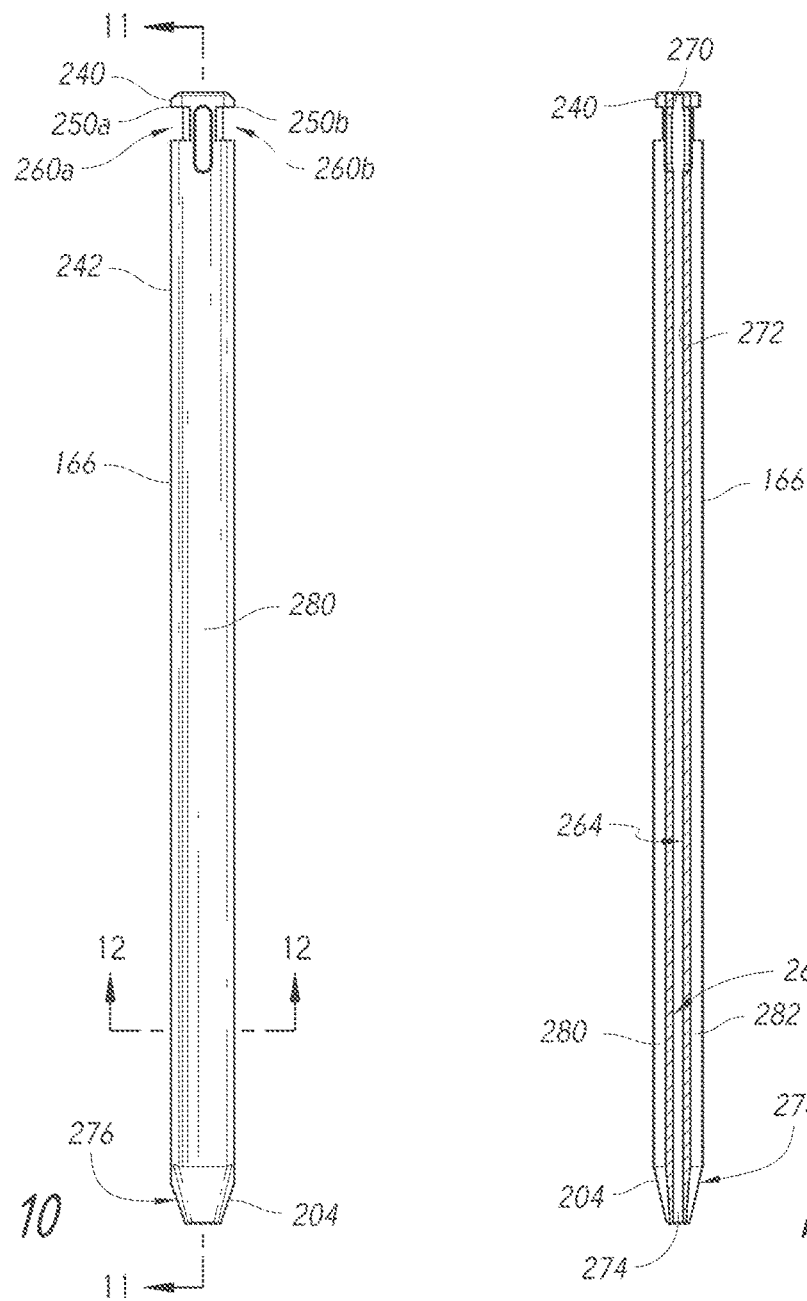
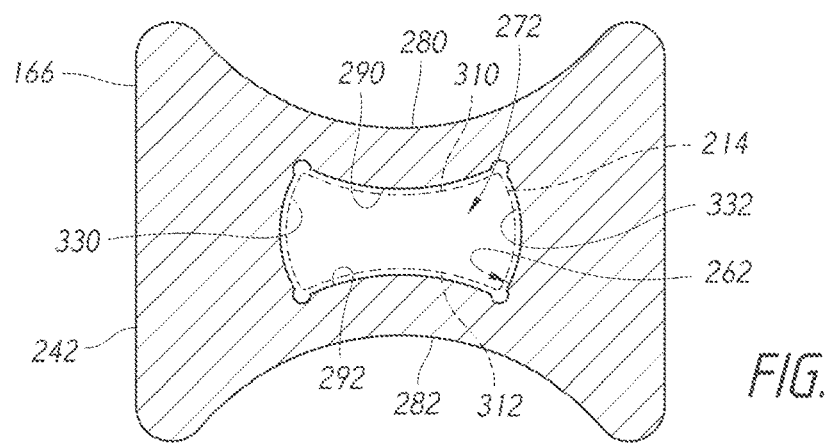
FIG. 10  FIG. 11  FIG. 12

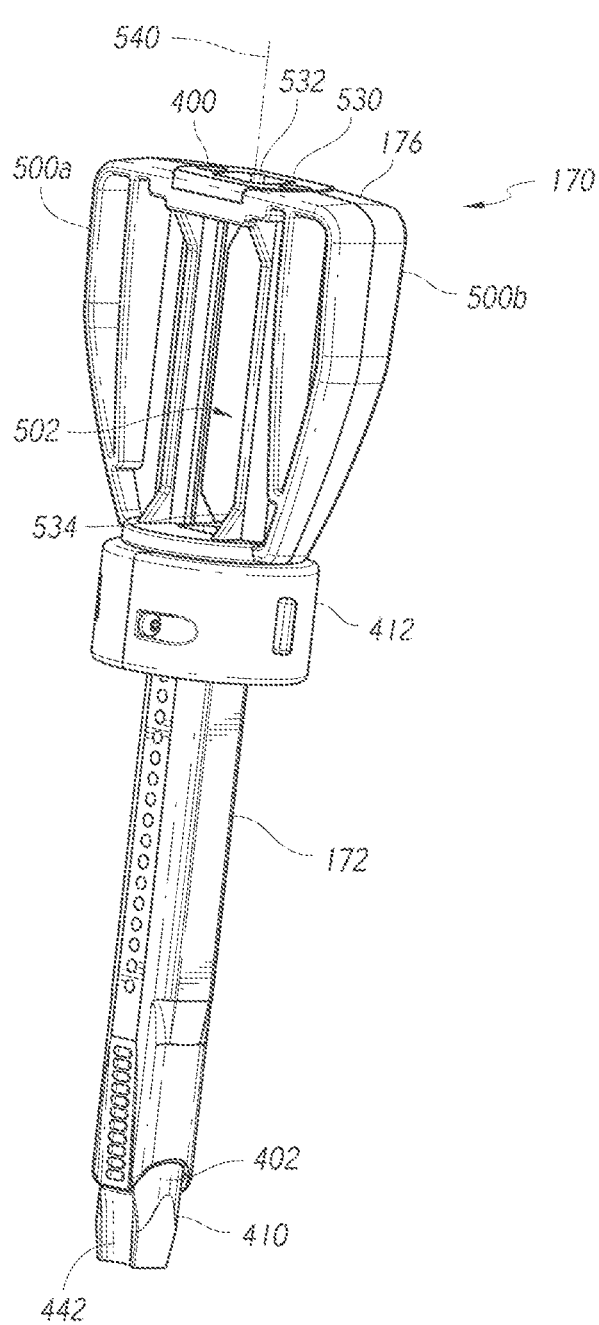
FIG. 17
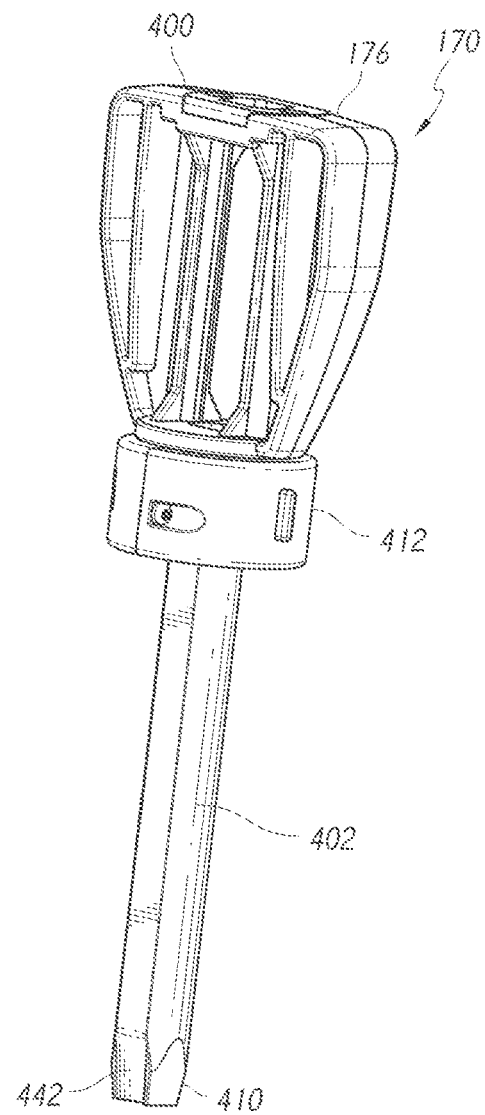
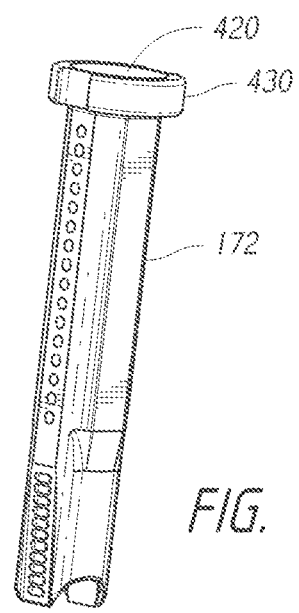
FIG. 18

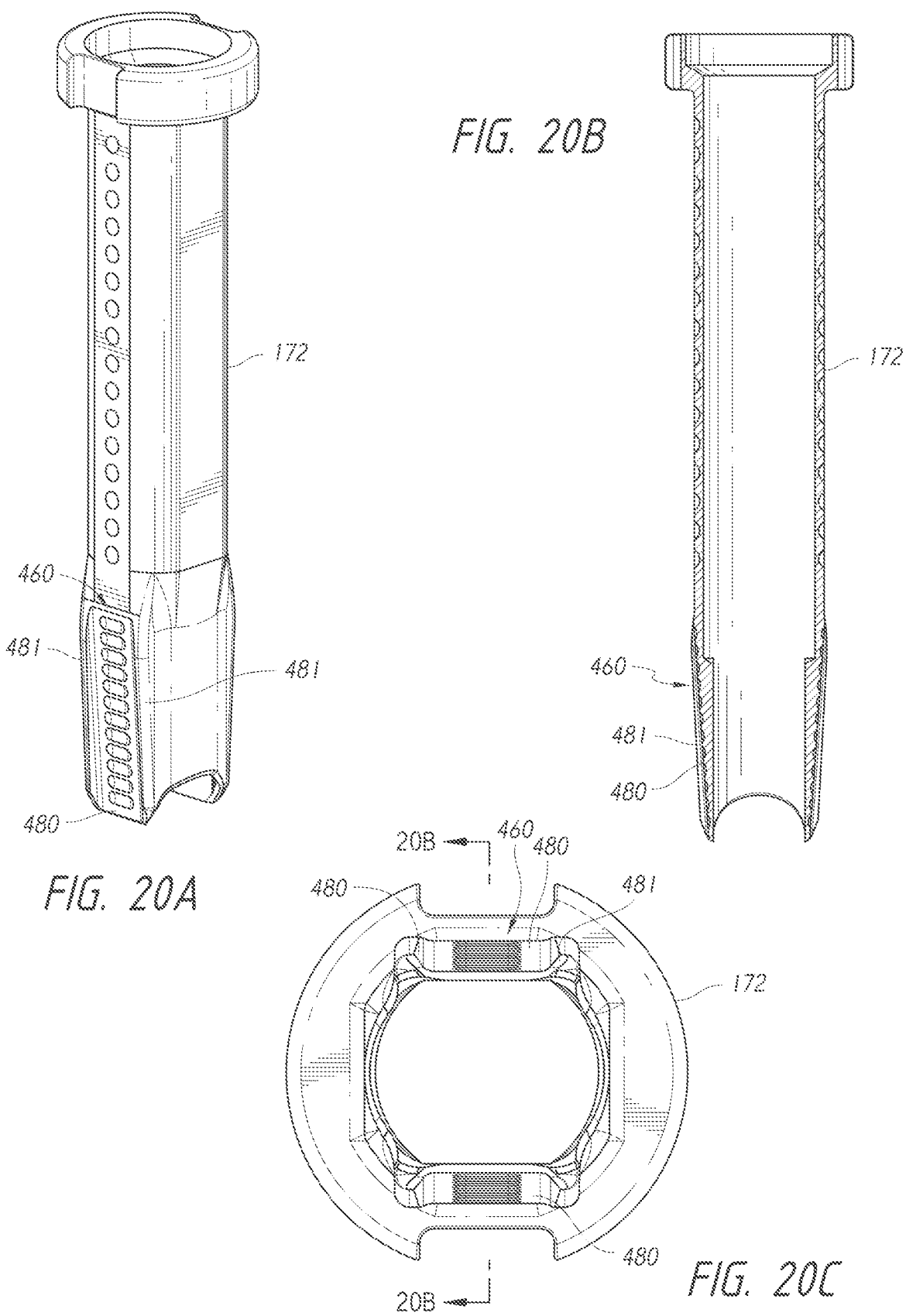

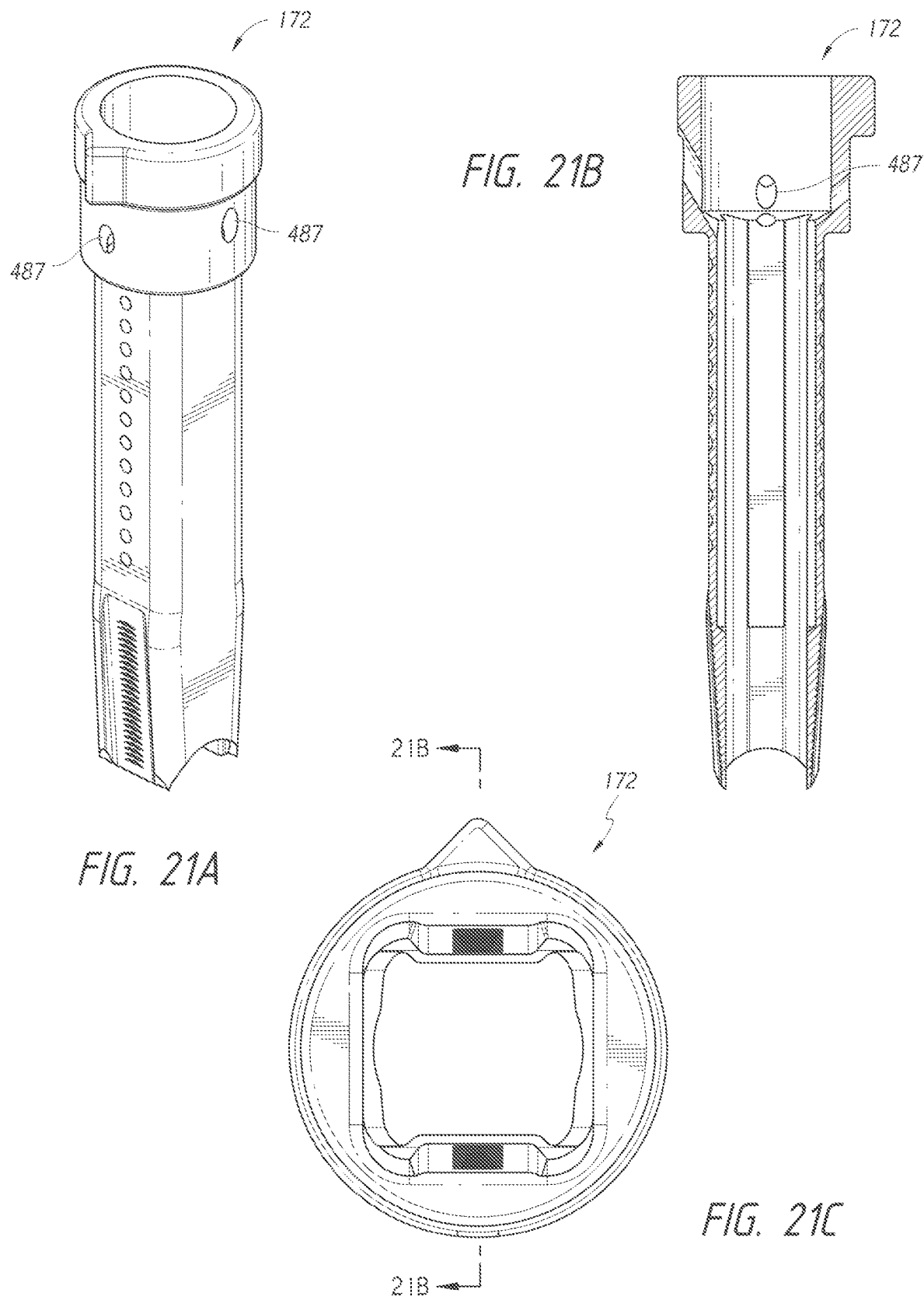

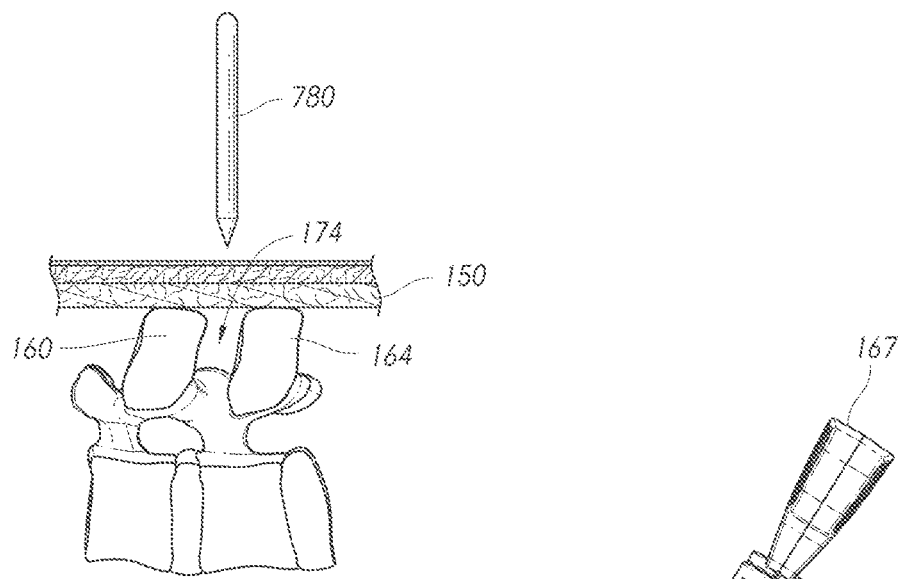
FIG. 31
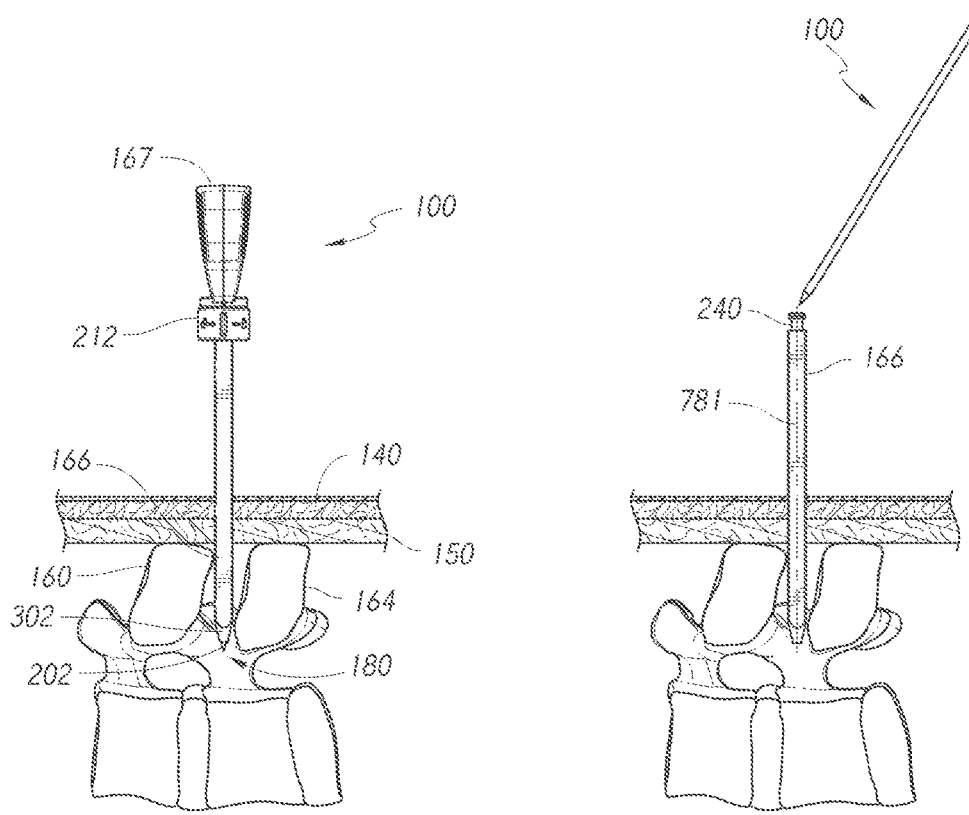
FIG. 32
FIG. 33

SPINAL NERVE DECOMPRESSION SYSTEMS, DILATION SYSTEMS, AND METHODS OF USING THE SAME

CROSS-REFERENCE TO RELATED APPLICATIONS

This application is a continuation of U.S. patent application Ser. No. 16/678,801, filed Nov. 8, 2019, which is a continuation of U.S. patent application Ser. No. 15/309,164, filed Nov. 4, 2016, which issued as U.S. Pat. No. 10,524,772, which is the national phase of PCT Application No. PCT/US2015/029537, filed May 6, 2015, which claims the benefit under 35 U.S.C. § 119(e) of U.S. Provisional Patent Application No. 61/990,030, filed on May 7, 2014 and U.S. Provisional Patent Application No. 62/060,965, filed on Oct. 7, 2014, all of which are incorporated by reference in their entireties.

TECHNICAL FIELD

The present disclosure relates generally to medical systems and, more particularly, to decompression systems, delivery instruments, visualization systems, and methods for treating spinal compression. In particular, the decompression systems can include dilation systems for providing access to treatment sites to treat spinal nerve compression.

BACKGROUND

Spinal nerve compression can be caused by narrowing of the spinal canal associated with arthritis (e.g., osteoarthritis) of the spine, degeneration of spinal discs, and thickening of ligaments. Arthritis of the spine often leads to the formation of bone spurs which can narrow the spinal canal and press on the spinal cord. In spinal disk degeneration, inner tissue of the disk can protrude through a weakened fibrous outer covering of the disk and can press on the spinal cord and/or spinal nerve roots. Ligaments located along the spine can thicken over time and press on the spinal cord and/or or nerve roots. Unfortunately, spinal nerve compression can cause lower back pain, hip pain, and/or leg pain and may also result in numbness, depending on the location of the compressed nerve tissue. For example, spinal stenosis that causes spinal cord compression in the lower back can cause numbness of the legs.

BRIEF DESCRIPTION OF THE DRAWINGS

FIG. 10 is a front view of an introducer dilator in accordance with an embodiment of the disclosure.

FIG. 11 is a cross-sectional view of the introducer dilator taken along line 11-11 of FIG. 10.

FIG. 12 is a cross-sectional view of the introducer dilator taken along line 12-12 of FIG. 10.

FIG. 17 is an isometric view of a cannula dilation assembly in accordance with an embodiment of the disclosure.

FIG. 18 is an exploded isometric view of the cannula dilation assembly of FIG. 17.

FIG. 20A is an isometric view of another embodiment of an instrument cannula.

FIG. 20B is a cross-sectional view of the instrument cannula taken along line 20B-20B of FIG. 20C.

FIG. 20C is a bottom view of the instrument cannula of FIG. 20A.

FIG. 21A is an isometric view of an instrument cannula suitable for use with an optical system in accordance with an embodiment of the disclosure.

FIG. 21B is a cross-sectional view of the instrument cannula taken along line 21B-21B of FIG. 21C.

FIG. 21C is a bottom view of the instrument cannula of FIG. 21A.

FIGS. 31-35 illustrate a method of accessing a treatment site and positioning an instrument cannula along a patient's spine.

DETAILED DESCRIPTION

Figure 1:
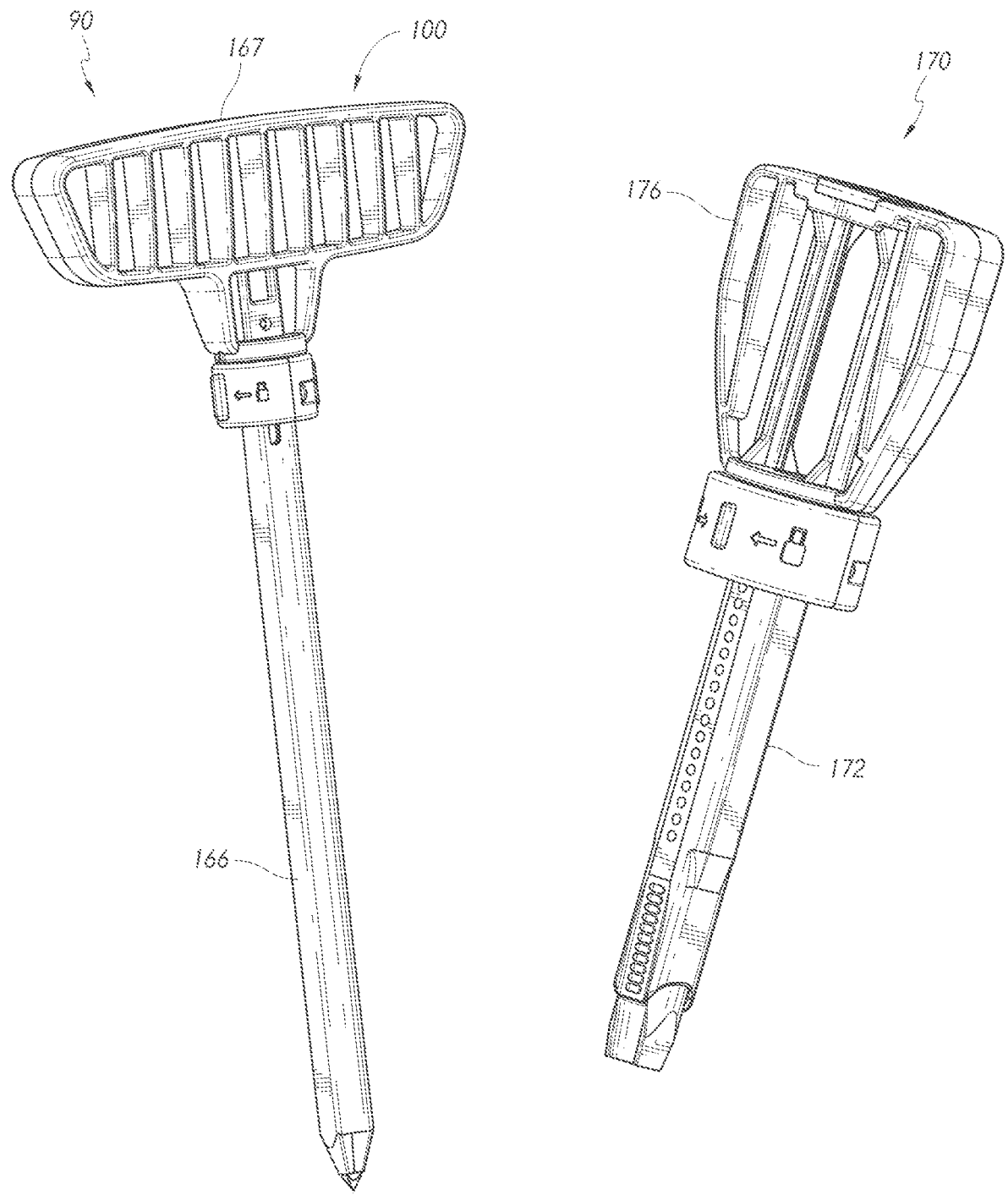
FIG. 1 is an isometric view of a dilation system in accordance with an embodiment of the disclosure.

The following disclosure describes various embodiments of treatment systems, delivery systems, dilations systems, visualization systems, and associated methods of use. At least some embodiments of a treatment system include a dilation system for accessing a treatment site. The dilation system can include a series of instruments sequentially delivered into the patient to sequentially dilate tissue and/or distract structures (e.g., adjacent vertebrae). One of the instruments can be a working cannula through which instruments can be passed. In one decompression procedure, a series of instruments can be delivered through the working cannula to alter tissue (e.g., crush, separate, cut, debulk, break, fracture, remove, or otherwise affect tissue). Visualization systems can be used to view the treatment site before and/or during tissue removal. Certain details are set forth in the following description and in FIGS. 1-47 to provide a thorough understanding of such embodiments of the disclosure. Other details describing well-known structures and systems often associated with, for example, dilating tissue, treating the spine, decompressing spinal nerves (e.g., nerves in the spinal cord, nerves in nerve roots exiting the spinal cord, etc.), or removing tissue are not set forth in the following description to avoid unnecessarily obscuring the description of various embodiments of the disclosure.

A. Overview

At least some embodiments are methods for treating spinal nerve compression and include making an incision and sequentially dilating tissue to position a working cannula in a patient. Sequential dilation can be used to gradually enlarge openings while minimizing or limiting trauma to tissue, thereby reducing recovery times and reducing patient discomfort. For example, sequential dilation provides an advantage in that it allows a surgeon to make an initially small incision, then gradually increase the size of the opening to the minimum size required for performing the surgical procedure, thus reducing tissue damage.

Instruments can be delivered through the working cannula to access targeted tissue. The targeted tissue can be, for example, bone, ligament, facet capsule, cyst material, and/or other tissue that contributes or causes stenosis, such as central and lateral recess stenosis. The decompression procedures can cause minimal or substantially no collateral tissue disruption and can be performed under anesthesia, such as local anesthesia. The method can further include, in some embodiments, delivering a spinal device (e.g., a spinal implant, a spacer device, prosthetics disk, or other spinal device) before and/or during tissue removal.

At least some embodiments are directed to a dilation system that includes a multiple dilation assemblies. Each dilation assembly can have an outer instrument and an inner instrument with a handle. The handle can be used to insert the dilation assembly into the subject. After inserting a dilation assembly into the subject, the inner instrument of that dilation assembly can be pulled from the outer instrument. A subsequent dilation assembly can be delivered over the outer instrument. This process can be repeated to deliver any number of dilation assemblies to perform a desired dilation procedure.

The dilation system, in some embodiments, includes first and second dilation assemblies. The first dilation assembly can include a first inner instrument with a handle and a first outer instrument. The first inner instrument can be configured to be separated from the first outer instrument when the first dilation assembly is in an unlocked configuration. The second dilation assembly can be moved over the first outer instrument when the second dilation assembly is in a locked configuration. The second dilation assembly can include a second inner instrument with a handle and a second outer instrument. The second inner instrument can be removed from the second outer instrument when the second dilation assembly is in an unlocked configuration.

In some embodiments, a dilation system for sequentially dilating anatomical features to provide access to a treatment site along a subject's spine includes first and second dilation assemblies. The first dilation assembly can include a first dilator and a needle device. The first dilator includes a distal end, a proximal end, and a lumen extending between the distal and proximal ends. The needle device includes a handle and a needle. The needle can have an elongate body coupled to the handle and a distal portion that protrudes from the distal end of the first dilator when the elongate body extends through the lumen of the first dilator. The second dilation assembly is configured to be moved over the first dilator after the needle device has been removed from the first dilator. In one embodiment, the second dilation assembly includes an instrument cannula and a second dilator. The instrument cannula includes a distal cannula end, a proximal cannula end, and an instrument passageway extending between the distal and proximal cannula ends. The second dilator includes a handle and a passageway through which the first dilator is capable of passing after the needle device has been removed from the first dilator.

A method for accessing a treatment site along a human subject's spine comprises inserting an introducer dilation assembly into a human subject such that the introducer dilation assembly is positioned between adjacent spinous processes of the subject. The introducer dilation assembly can include an introducer dilator and a needle assembly positioned in the introducer dilator. The needle assembly can be removed from the introducer dilator after the introducer dilation assembly has been inserted into the subject. After removing the needle assembly from the introducer dilator, a cannula dilation assembly can be moved over the introducer dilator to position the cannula dilation assembly between the spinous processes. The cannula dilation assembly can include an instrument cannula and a cannula dilator positioned in the introducer dilator. The cannula dilator can be removed from the instrument cannula after the cannula dilation assembly has been inserted into the subject.

In further embodiments, a dilation system includes at least one dilator that includes a proximal portion and a tapered distal portion interconnected by an elongated body portion. The tapered distal portion can be configured for separating or splitting tissue (e.g., ligamentous tissue) for creating a pathway (e.g., a posterior midline pathway through the supraspinous ligament), as well as for distracting spinous processes. Two oppositely located and longitudinally extending channels or grooves are formed in the outer surface of the dilator for stabilizing the dilator with respect to the spinous processes. An accompanying cannula together with the dilator form an assembly for the distraction of the adjacent spinous processes, stabilization of the spinous processes with respect to the system, and/or creation of a suitable delivery path for the implantation of an interspinous spacer. In one embodiment, multiple dilators can be used to provided sequentially dilation. The dilators can be delivered over one another to gradually dilate tissue.

At least some embodiments are directed to a reamer instrument including a reaming assembly and a positioner element. The reaming assembly includes an outer reamer member having a lateral reaming element, an elongate body, and a lumen extending between first and second ends of the outer reamer member. The reaming assembly can also include an inner reamer member including a reaming tip and a rod. The rod is positioned in the lumen. The positioner element is connected to the inner reamer member. The positioner element can be moved to position at least a portion of the reaming tip outside of the outer reamer member and an atraumatic position for positioning the reaming tip within the outer reamer member.

At least one embodiment is directed to surgical instruments that can be delivered through a cannula. The surgical instruments can include a handheld reaming instrument that includes a reaming assembly and a handle assembly. The reaming assembly can comprise an outer reamer member and an inner reamer member. The handle assembly can include a handle and a depth stop mechanism. The depth stop mechanism can be manually moved to adjust the maximum depth of penetration of the reaming assembly to avoid trauma to non-targeted tissue. The depth stop mechanism, in some embodiments, includes a locking assembly and a depth stop member. The locking assembly can have a locked configuration for holding the depth stop member and an unlocked configuration for moving the depth stop member. Other surgical instruments can be, without limitation, tissue removal instruments, debulker instruments, reamer instruments, or other types of instruments.

In some embodiments, a method for performing a procedure on a subject comprises positioning a visualization instrument relative to a cannula to view a vertebral column of the subject. The spinal decompression procedure can include, without limitation, crushing, separating, cutting, debulking, breaking, fracturing, removing, or otherwise altering tissue using decompression instruments sequentially positioned via the cannula. In non-fluoroscopic procedures, a physician can look through the lumen of the cannula to directly view the treatment site. The visualization instrument can illuminate and view the treatment site to help identify tissue (e.g., targeted tissue, non-targeted tissue, etc.), features of interest, or the like. In non-fluoroscopic procedures, the physician can use both direct viewing and viewing via fluoroscopy.

The visualization instrument, in some embodiments, can be mechanically coupled to the cannula such that the cannula and visualization instrument are moved together. For example, a coupler can fixedly couple the visualization instrument to the cannula. In one embodiment, the coupler can include a clamp having an open configuration for repositioning the visualization instrument and a closed configuration for holding the visualization instrument. In some embodiments, the visualization instrument can be positioned in an access feature in the form of a through-hole in a sidewall of the cannula and can include one or more light sources capable of outputting light for illuminating a treatment site distal to the cannula. The illustrated target tissue can be viewed with the naked eye. Additionally, the visualization instrument can include one or more imaging devices, such as cameras, for viewing on an electronic display (e.g., a color monitor).

In some embodiments, a visualization system can be used to view tissue to, among other things, prevent damaging non-targeted tissue. The visualization system can provide viewing of decompression instruments and/or treatment sites to help position decompression instruments. In one embodiment, the visualization system can be used for directly viewing of the treatment site and/or distal end of the decompression instrument. In other embodiments, visualization systems can provide viewing via a display, such as a color monitor.

Visualization systems can be used in decompression procedures for treating spinal nerve compression (e.g., spinal cord compression, spinal nerve root compression, or the like), spinal disk herniation, osteoporosis, stenosis, or other diseases or conditions. In one embodiment, a tissue removal instrument is used to perform a spinal cord decompression procedure, which can include removing bone from one or more vertebrae, separating the ligamentum flavum from one or more vertebrae, cutting or debulking the ligamentum flavum, and/or removing loose tissue while a physician views the treatment site using the visualization system.

The terms "distal" and "proximal" within this description, unless otherwise specified, reference a relative position of the portions of an systems, instruments, and/or associated access devices with reference to an operator and/or a location in the patient. For example, in referring to visualization systems described herein, the term "proximal" can refer to a position closer to the operator, and the term "distal" can refer to a position that is more distant from the operator.

B. Decompression Systems

FIG. 1 is an isometric view of a dilation system 90 for sequentially dilating anatomical features of a human subject in accordance with an embodiment of the disclosure. The dilation system 90 can include an introducer or inner dilation assembly 100 ("introducer dilation assembly 100") for initially dilating anatomical features and an outer dilation assembly 170 for further dilating the anatomical features. The introducer dilation assembly 100 can include a hollow introducer dilator 166 and a needle device 167 extending through the introducer dilator 166. The outer dilation assembly 170 can include a dilator device 176 and a working or instrument cannula 172 ("instrument cannula 172") and can be delivered over the introducer dilator 166 after the needle device 167 has been removed from the introducer dilator 166. The introducer dilation assembly 100 and outer dilation assembly 170 can sequentially distract adjacent vertebrae to achieve a large amount of distraction while managing the pressure applied to the vertebrae.

Figure 2:
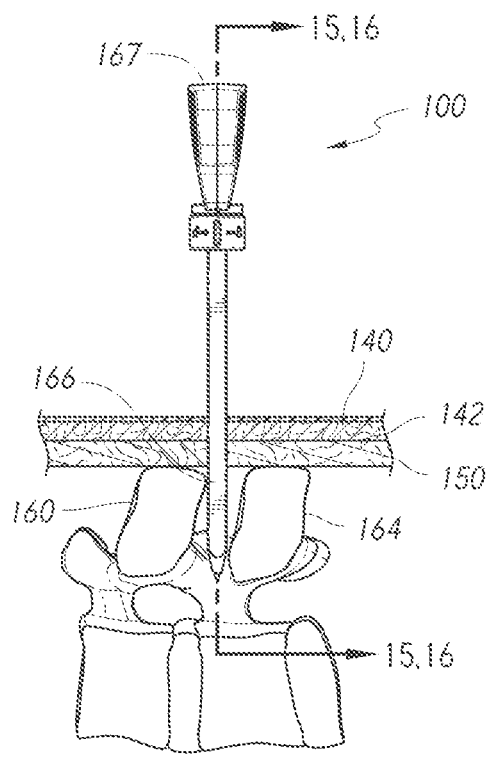
FIGS. 2-7 illustrate a method of performing a spinal decompression procedure using the dilation system of FIG. 1 in accordance with an embodiment of the disclosure.
Figure 3:
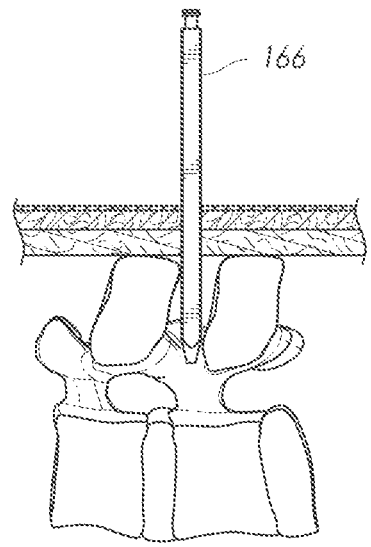

FIGS. 2-5 illustrate a dilation procedure performed using the dilation system 90 of FIG. 1. FIG. 2 shows the introducer dilation assembly 100 after it has been driven into the subject. The introducer dilation assembly 100 can extend through a subject's skin 140, subcutaneous tissue 142, and supraspinous ligament 150 and, in midline procedures, can be positioned generally between adjacent spinous processes 160, 164. FIG. 3 shows the introducer dilator 166 after the needle device 167 (FIG. 2) has been removed therefrom.

Figure 4:
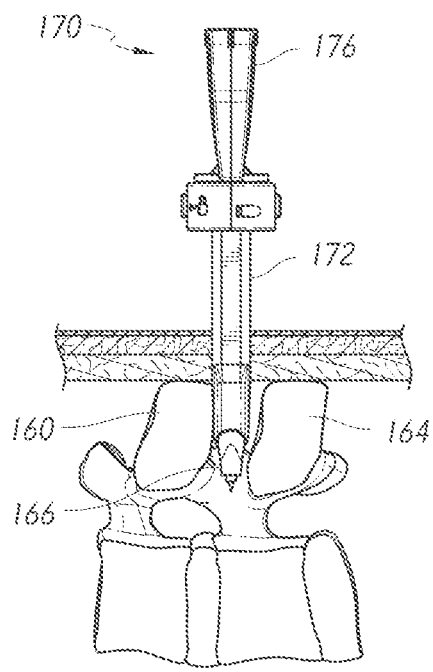
Figure 5:
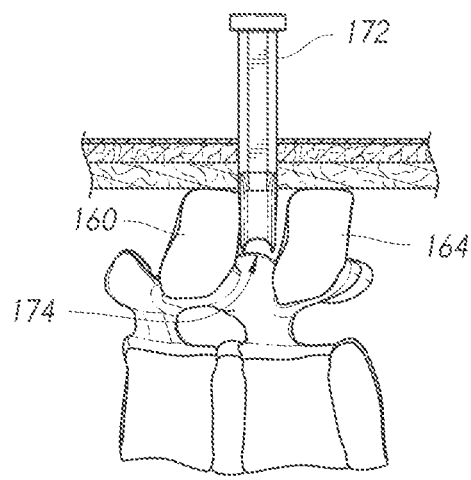

FIG. 4 shows the dilation assembly 170 after it has been delivered over the introducer dilator 166 to position the instrument cannula 172 between the spinous processes 160, 164. FIG. 5 shows the instrument cannula 172 after the introducer dilator 166 has been removed from the dilation assembly 170 and after the dilator device 176 has been pulled out of the instrument cannula 172. The cannula 172 can hold apart the spinous processes 160, 164 to maintain a desired amount of distraction for enlarging an interspinous space.

Figure 6:
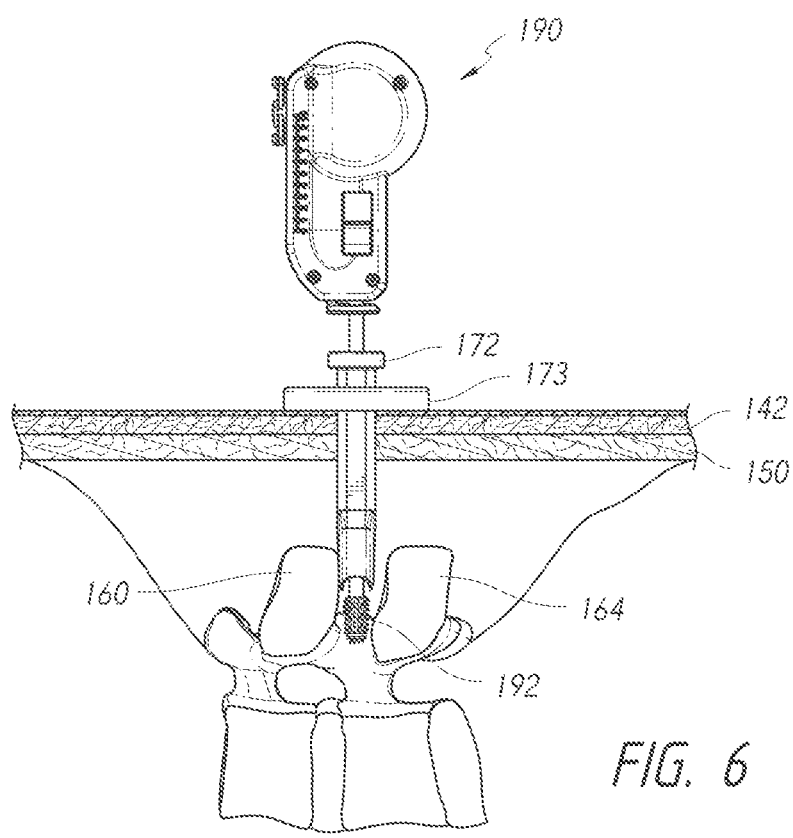
Figure 7:
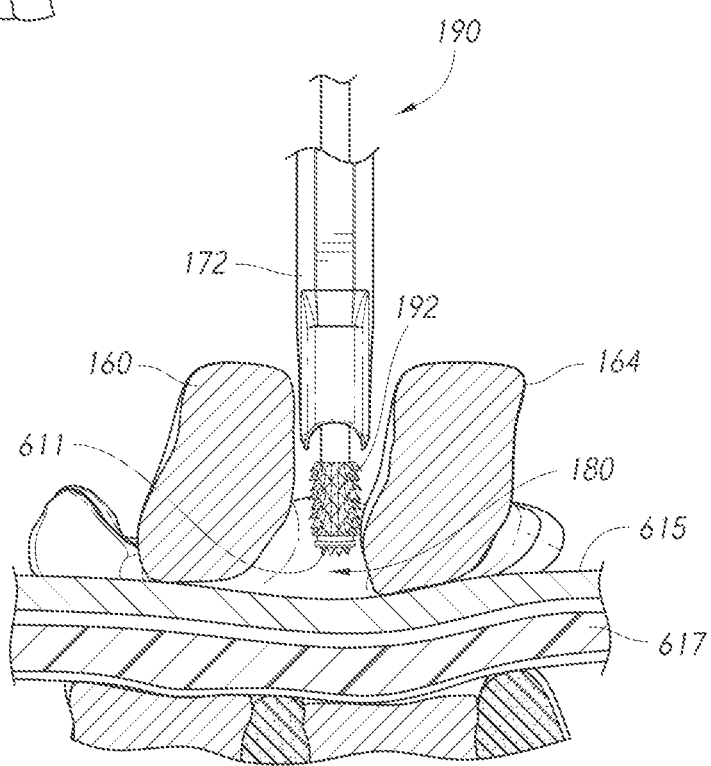

FIGS. 6 and 7 illustrate a method of performing at least a portion of the decompression procedure using the instrument cannula 172 held by a cannula holder 173. A surgical instrument in the form of a reamer instrument 190 has a distal end 192 that can scrape, abrade, or otherwise alter tissue within, adjacent to, or along the subject's spine. Other instruments can be delivered through the cannula 172 to perform a wide range of decompression procedures or other type of procedure. Details of the instruments and features shown in FIGS. 1-7 are discussed below.

Figure 8:
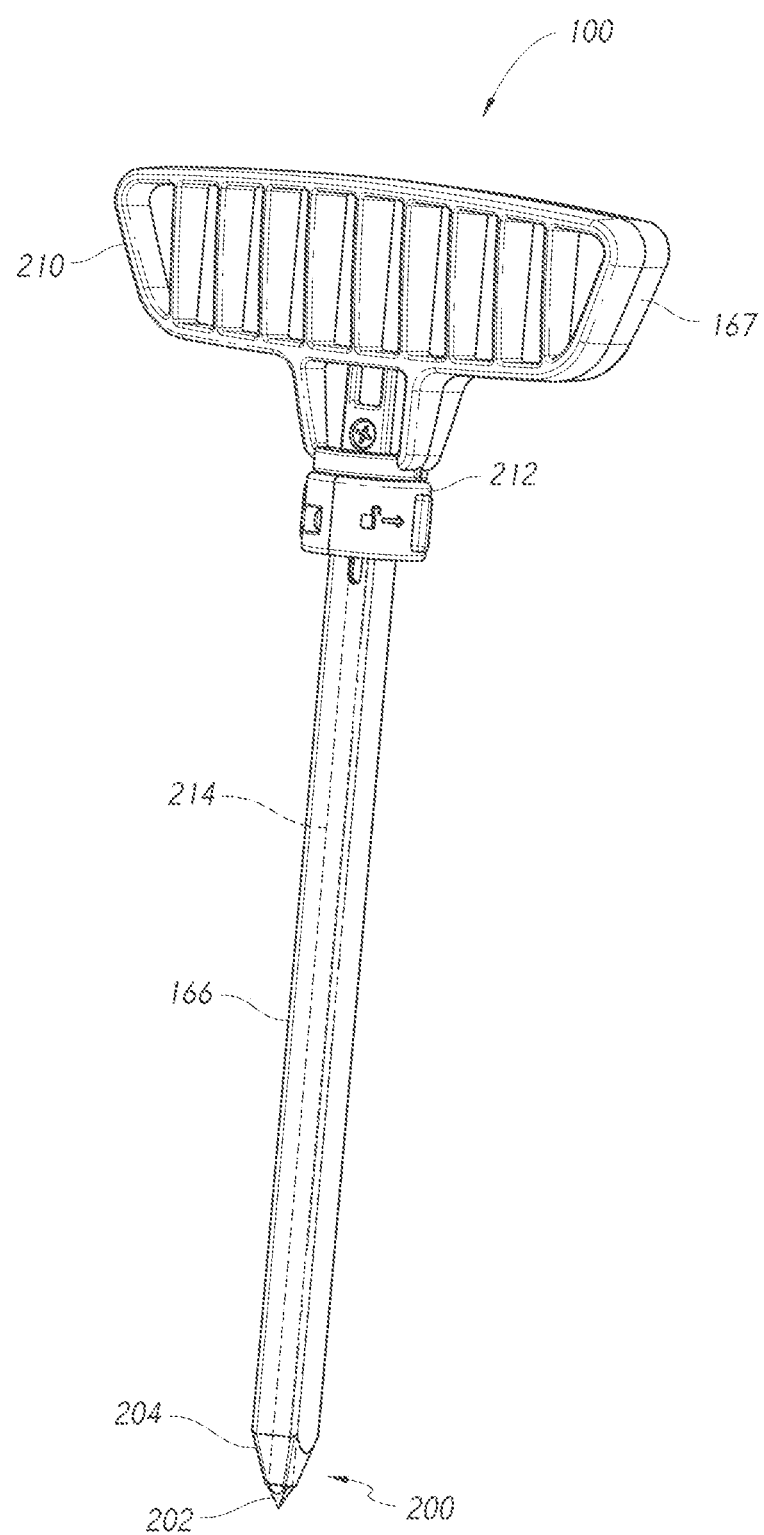
FIG. 8 is an isometric view of an introducer dilation assembly in accordance with an embodiment of the disclosure.
Figure 9:
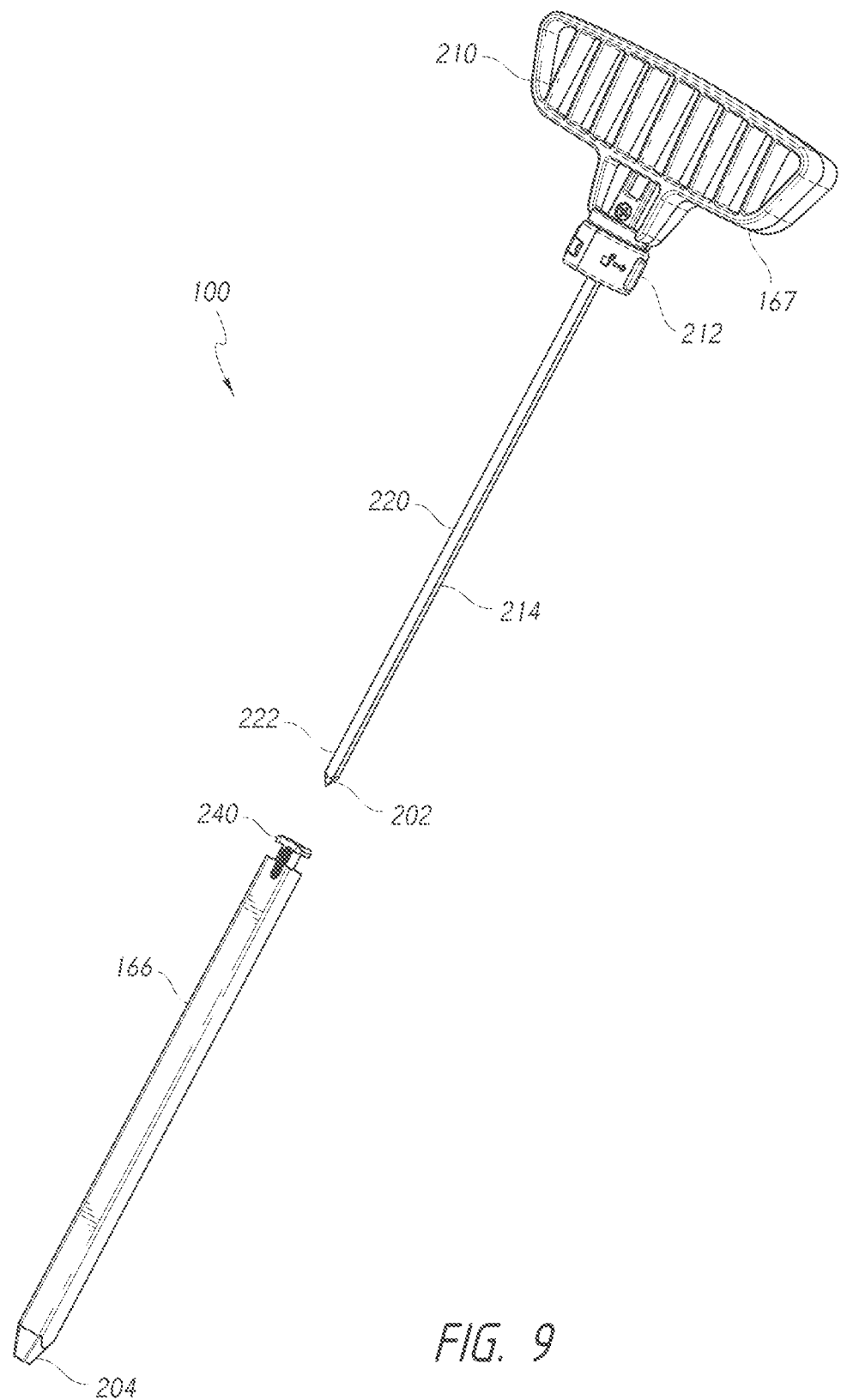
FIG. 9 is an exploded isometric view of the introducer dilation assembly of FIG. 8.

FIG. 8 is an isometric view of the introducer dilation assembly 100 with a relatively sharp tip or distal portion 200. FIG. 9 is an exploded isometric view of the introducer dilation assembly 100. The needle device 167 can include a handle 210, a locking mechanism 212, and a needle 214. The handle 210 can be conveniently gripped by a user to push the introducer dilation assembly 100 into the subject. The locking mechanism 212 can have a locked configuration for holding the introducer dilator 166 and an unlocked configuration for releasing the introducer dilator 166. Referring now to FIG. 9, the needle 214 can be directly or indirectly coupled to the handle 210 and can include an elongate body 220 and a distal portion 222 with a sharp needle tip 202. To assemble the introducer dilation assembly 100, the needle tip 202 can be inserted into the introducer dilator 166. The needle 214 can be advanced along the introducer dilator 166 until a proximal end 240 of the introducer dilator 166 is received by the locking mechanism 212. The locking mechanism 212 can be moved from an unlocked configuration to a locked configuration to securely hold the introducer dilator 166. Details of the introducer dilator 166 are discussed in connection with FIGS. 10-12, details of the needle device 167 are discussed in connection with FIGS. 13 and 14, and details of the locking mechanism 212 are discussed in connection with FIGS. 15 and 16.

FIG. 10 is a front view of the introducer dilator 166 in accordance with an embodiment of the present disclosure. FIG. 11 is a longitudinal cross-sectional view of the introducer dilator 166 taken along line 11-11 of FIG. 10. FIG. 12 is a cross-sectional view of the introducer dilator 166 taken along line 12-12 of FIG. 10. Referring now to FIG. 10, the introducer dilator 166 can include a tapered distal end 204, proximal end 240, and main body 242. The distal end 204 can include an opening 274 (FIG. 11) and a smooth outer surface 276 and can have a generally frusto-conical shape, truncated pyramidal shape, or other shape suitable for passing through an incision, spreading or stretching tissue, dilating openings or gaps, or the like. The proximal end 240 can include flanges 250a, 250a that define receiving windows 260a, 260b, respectively. Referring now to FIGS. 11 and 12, an inner surface 262 defines a passageway 272 extending between the openings 270, 274. The passageway 272 is configured to slidably receive the needle 214 (FIG. 9).

FIG. 12 shows two oppositely positioned outer alignment features in the form of outer channels 280, 282 that extend longitudinally along the main body 242. The channels 280, 282 can have U-shaped profiles, V-shaped profiles, arcuate profiles (e.g., concave configurations), or other profiles suitable for engaging vertebrae, spinous processes, or other tissue. As shown in FIG. 10, the channel 280 can extend from the distal end 204 toward the proximal end 240 to allow tissue to slide along the entire length of the introducer dilator 166 or portion thereof. Inner alignment features 290, 292 can be in the form of longitudinally-extending convex portions located on opposites sides of the passageway 272. The number, location, and orientation of alignment features can be selected based on the instruments used with the introducer dilator 166.

Figure 13:
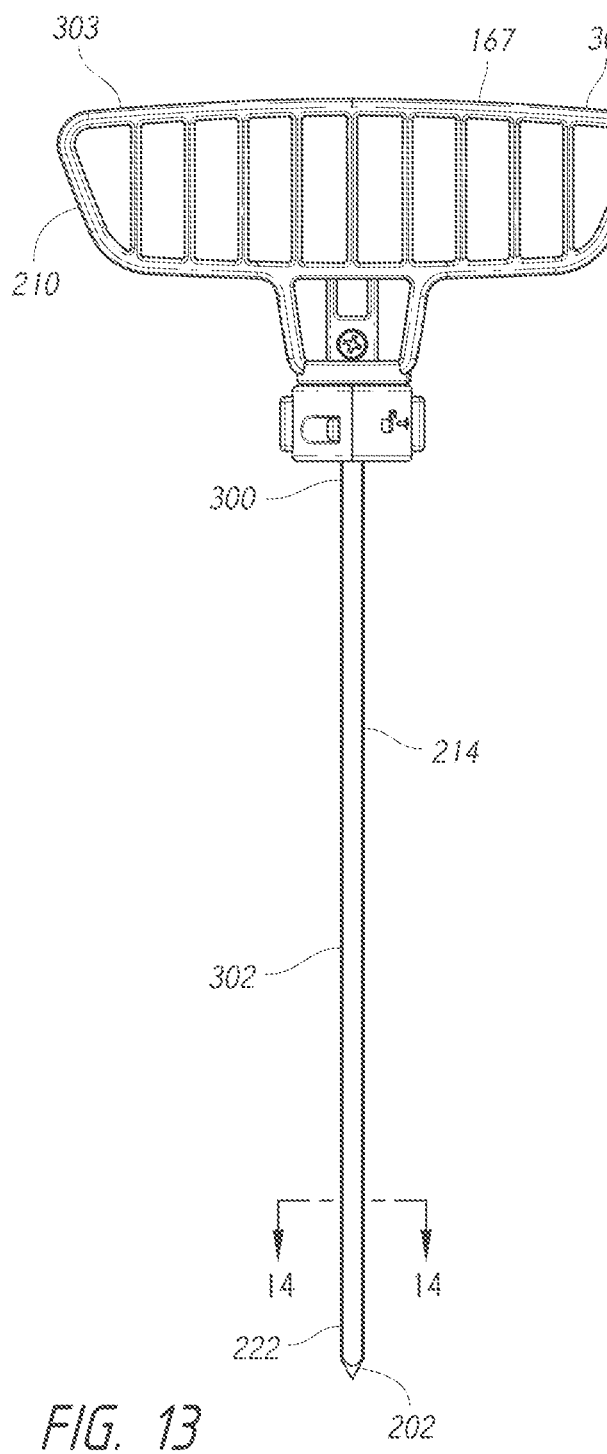
FIG. 13 is a front view of a needle device with a handle suitable for use with the introducer dilator of FIGS. 10-12 in accordance with an embodiment of the disclosure.

FIG. 13 is a front view of the needle device 167 in accordance with an embodiment of the disclosure. The needle 214 can include the needle tip 202, a proximal end 300, and a main body 302. The proximal end 300 can be fixedly or detachably coupled to the handle 210, illustrated as a T-shaped handle that a user can comfortably grip by wrapping his or her fingers about handle end portions 303, 304. Other types of handles can also be used. The needle tip 202 may be relatively sharp and may have a knife-like edge that can pierce tissue (e.g., ligaments) without first using a sharp edge and can therefore be used for percutaneous procedures. In other embodiments, the needle tip 202 can have a conical shape, a pyramidal shape, or other suitable shape for piercing tissue.

Figure 14:
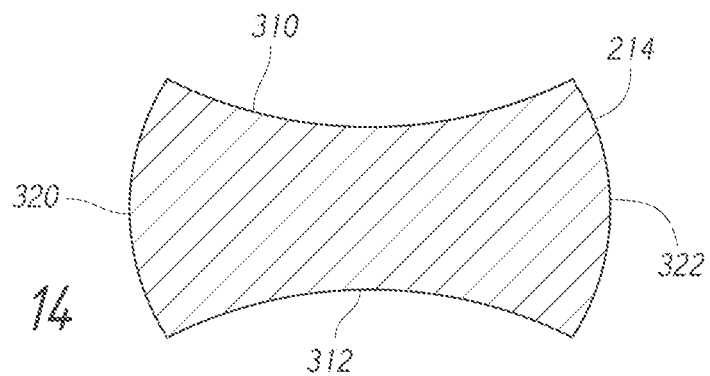
FIG. 14 is a cross-sectional view of the needle device taken along line 14-14 of FIG. 13.

FIG. 14 is a cross-sectional view of the needle 214 taken along line 14-14 of FIG. 13. Two oppositely positioned alignment features in the form of channels 310, 312 extend longitudinally along the main body 302. Referring to FIG. 13, the channels 310, 312 can have arcuate profiles, U-shaped profiles, V-shaped profiles, or other suitable convex or concave profiles for engaging the alignment features 290, 292 (FIG. 12) of the introducer dilator 166. In some embodiments, the channels 310, 312 can slidably engage respective alignment features 290, 292 of the introducer dilator 166 to rotationally lock together the needle 214 and introducer dilator 166. Alignment features in the form of longitudinally-extending convex portions 320, 322 located on opposites sides of the needle 214 can slidably engage alignment features in the form of convex portions 330, 332 (FIG. 12). In various embodiments, the needle 214 can have a polygonal cross-sectional profile (e.g. a square profile, a rectangular profile, etc.), an elliptical profile, or other profile suitable for maintaining desired alignment with introducer dilators or other components.

Figure 15:
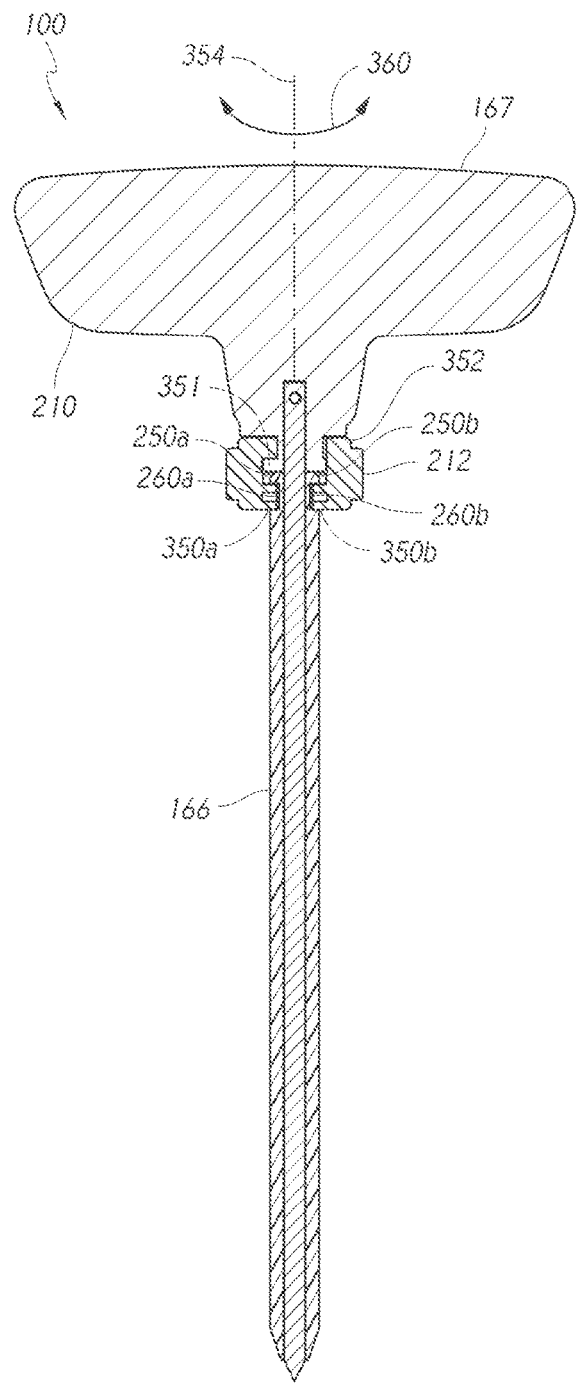
FIG. 15 is a cross-sectional view of the introducer dilation assembly taken along line 15-15 of FIG. 2 with a locking mechanism in a locked configuration in accordance with an embodiment of the disclosure.
Figure 16:
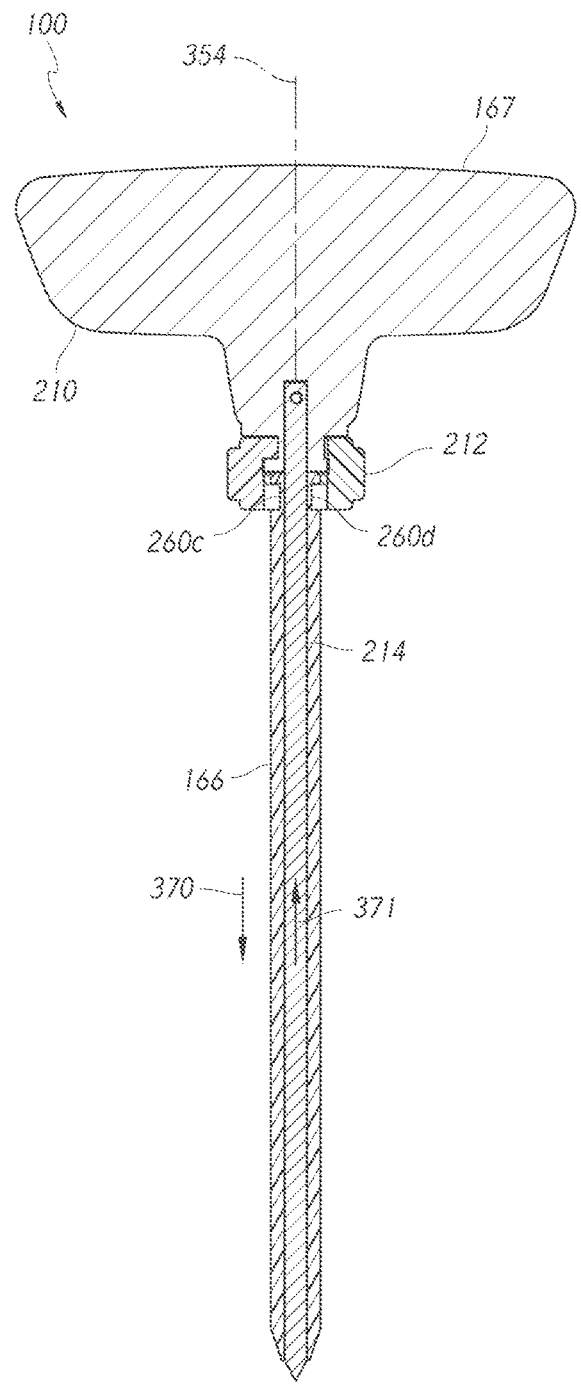
FIG. 16 is a cross-sectional view of the introducer dilation assembly taken along line 16-16 of FIG. 2 with the locking device in an unlocked configuration.

FIGS. 15 and 16 are longitudinal cross-sectional views of the introducer dilation assembly 100 with the locking mechanism 212 in locked and unlocked configurations, respectively. Referring to FIG. 15, flanges 250a, 250b of the introducer dilator 166 can be held between upper surfaces of the retaining elements in the form of flanges 350a, 350b and an abutment 351 of the handle 210. To move the locking mechanism 212 to the unlocked configuration, a cylindrical body 352 of the locking mechanism 212 can be rotated about an axis of rotation 354 (indicated by arrows 360) to move the flanges 350a, 350b. FIG. 16 shows the locking mechanism 212 in the unlocked configuration after the flanges 350a, 350b (FIG. 15) have been moved out of the windows 260a, 260b. To separate the introducer dilator 166 and the needle device 167, the user can push the introducer dilator 166 distally (indicated by arrow 370) away from the handle 210 and/or pull the needle 214 proximally (indicated by arrow 371) relative to the introducer dilator 166. Other types of locking mechanisms can be used and may include, without limitation, one or more pins, threaded members, or other features suitable for coupling together and releasing components.

FIG. 17 is an isometric view of the outer dilation assembly 170 in accordance with an embodiment of the disclosure. FIG. 18 is an exploded isometric view of the outer dilation assembly 170. Referring to FIGS. 17 and 18 together, the dilator device 176 can include a dilator handle 400, a locking mechanism 412, and an elongate dilator 402 with a distal end 410. The locking mechanism 412 has a locked configuration for coupling together the instrument cannula 172 and the dilator device 176 and an unlocked configuration for separating the instrument cannula 172 and the dilator device 176.

To assemble the outer dilation assembly 170 of FIG. 18, the distal end 410 of the elongate dilator 402 can be inserted into an entrance opening 420 of the instrument cannula 172. The elongate dilator 402 can be moved along the cannula 172 until a head 430 of the cannula 172 is received by the locking mechanism 412. The locking mechanism 412 can be moved from the unlocked configuration to a locked configuration to hold together the dilation assembly 170 and instrument cannula 172 such that the distal end 410 protrudes from the instrument cannula 172 to expose sloped channels 442.

Figure 19A:
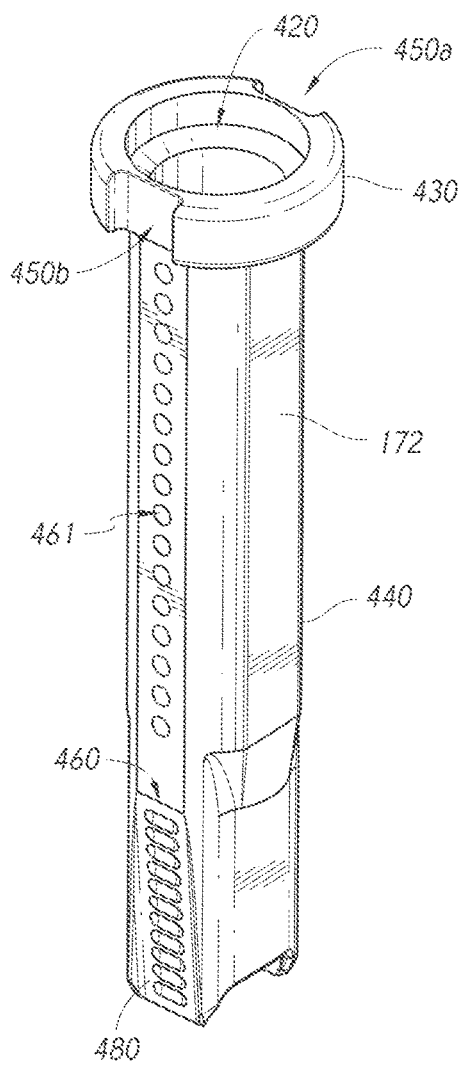
FIG. 19A is an isometric view of an instrument cannula in accordance with an embodiment of the disclosure.
Figure 19B:
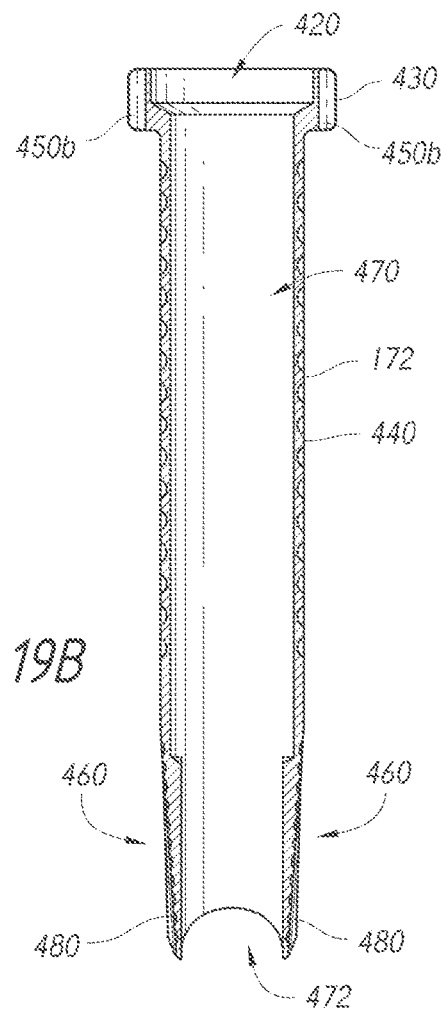
FIG. 19B is a cross-sectional view of the instrument cannula taken along line 19B-19B of FIG. 19C.
Figure 19C:
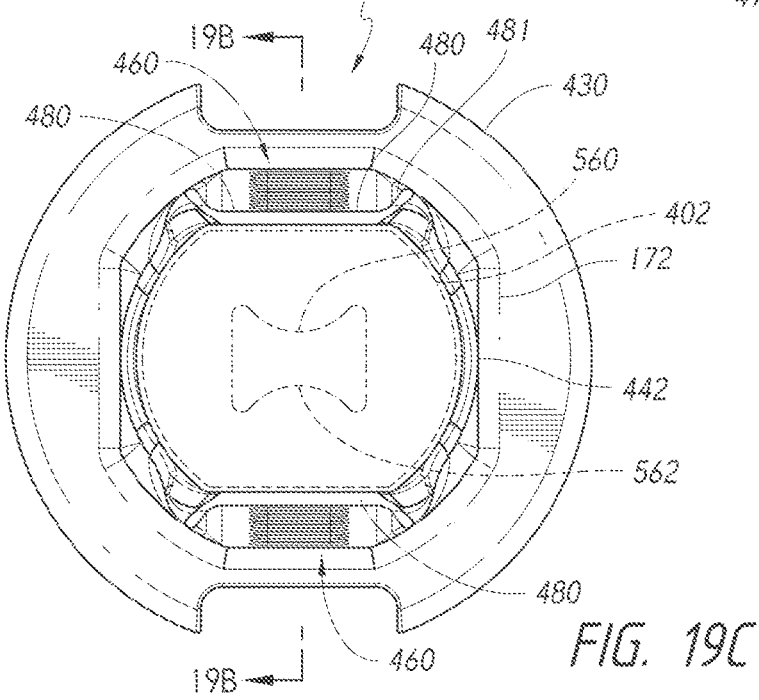
FIG. 19C is a bottom view of the instrument cannula of FIG. 19A.

FIG. 19A is an isometric view of the instrument cannula 172 in accordance with an embodiment of the disclosure. FIG. 19B is a cross-sectional view of the instrument cannula 172 taken along line 19B-19B of FIG. 19C. FIG. 19C is a bottom view of the instrument cannula 172. The instrument cannula 172 can include the head 430, distal end 410, and main body 440 therebetween. The head 430 defines the opening 420 (FIGS. 19A and 19B) and keying features 450a, 450b (collectively "keying features 450"). An instrument passageway 470 (FIG. 19B) extends between the opening 420 and the opening 472 and is configured to receive instruments.

The instrument cannula 172 can include positioning features 460 located along the bottom of guide channels 480. The positioning features 460 can be recesses (e.g., spherical recesses, elongated recesses, etc.), protrusions, grooves, notches, or other features suitable for engaging tissue or bone. The illustrated embodiment includes eleven positioning features 460, but a greater or lesser number of positioning features can be selected based on a desired number of available preferential positions. In some embodiments, the instrument cannula 172 can include an array of locators 461 for positioning relative to a holder, such as the clamp assembly discussed in connection with FIGS. 37-42. The guide channels 480 can have U-shaped cross-sectional profiles, V-shaped cross-sectional profiles, or other suitable profiles for interacting with anatomical features. The guide channels 480 can be sloped or angled to provide for distraction.

FIG. 20A is an isometric view of an instrument cannula in accordance with an embodiment of the disclosure. FIG. 20B is a cross-sectional view of the instrument cannula taken along line 20B-20B of FIG. 20C. FIG. 20C is a bottom view of the instrument cannula of FIG. 20A. The description of the cannula 172 of FIGS. 19A-19C applies equally to the cannula 172 of FIGS. 20A-20C, except as detailed below. The cannula 172 has twelve (illustrated), thirteen, fourteen, or more positioning features 460 located along a central region of the guide channels 480. Guide rails 481 of FIGS. 20A and 20B are higher and longer than guide rails 481 of FIG. 19C. In some embodiments, most or all of the positioning features 460 of FIGS. 20A-20C are positioned between the guide rails 481. The number, spacing, dimensions of the positioning features 460 can be selected based on the positions and configurations of the anatomical structures to be received, and the spacing and dimensions (e.g., lengths, heights, etc.) of the guide rails 481 can be selected based on the anatomical features to be moved along the guide channels 480.

FIG. 21A is an isometric view of an instrument cannula 172 in accordance with an embodiment of the disclosure. FIG. 21B is a cross-sectional view of the instrument cannula taken along line 21B-21B of FIG. 21C. FIG. 21C is a bottom view of the instrument cannula of FIG. 21A. The description of the cannula 172 of FIGS. 19A-20C applies equally to the cannula 172 of FIGS. 21A-21C, except as detailed below. Referring to FIG. 21A, the cannula 172 has positioning features (illustrated as notches) located along the guide channels. Instruments can be passed through access features 487 circumferentially spaced about the cannula 172. The access features 487 can be ports, through-holes, or other features through which visualization instruments, surgical instruments, or other instruments can be passed. For example, illumination instruments can be inserted through the ports 487 to illuminate tissue distal to the cannula 172.

Figure 22:
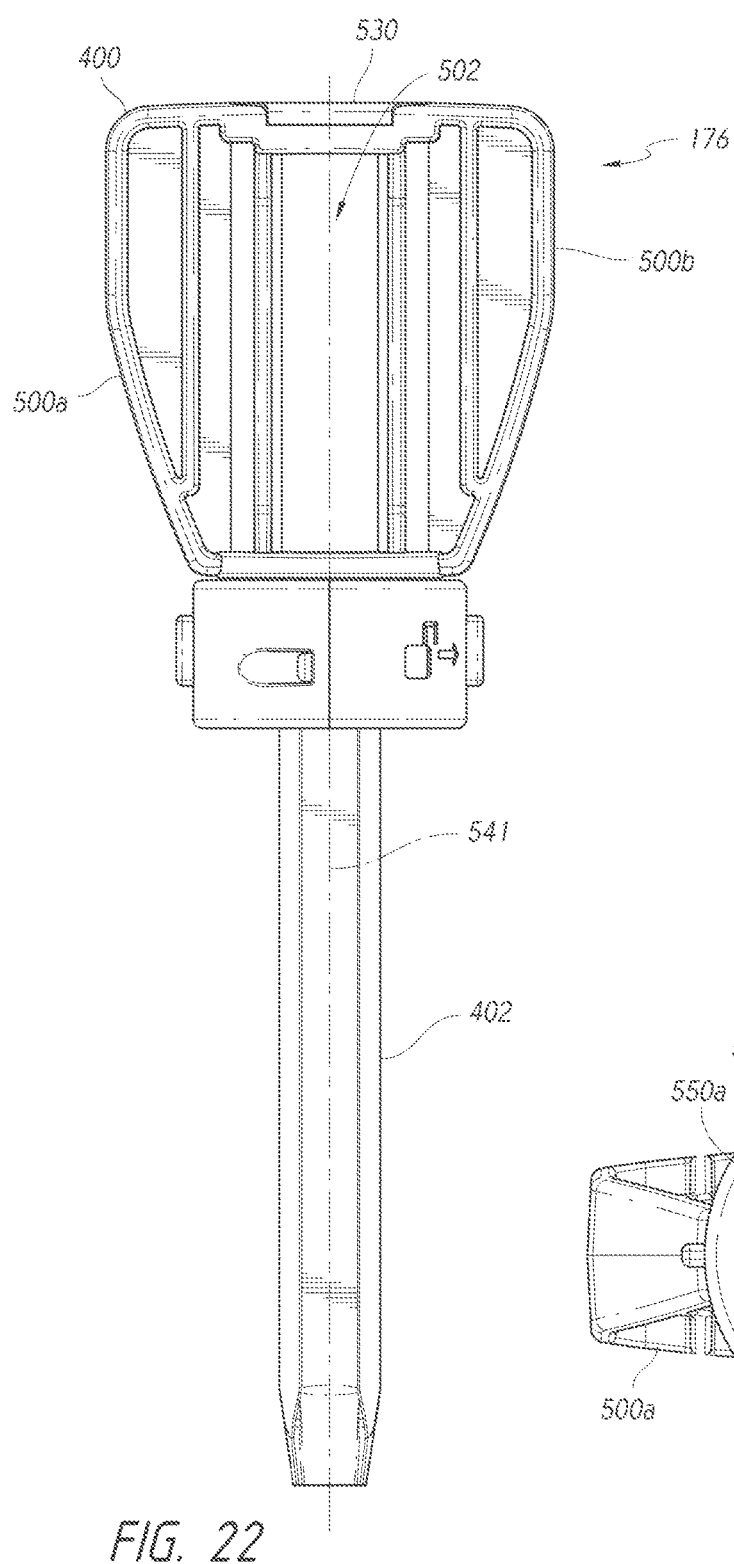
FIG. 22 is a front view of a dilation device with a handle in accordance with an embodiment of disclosure.
Figure 23:
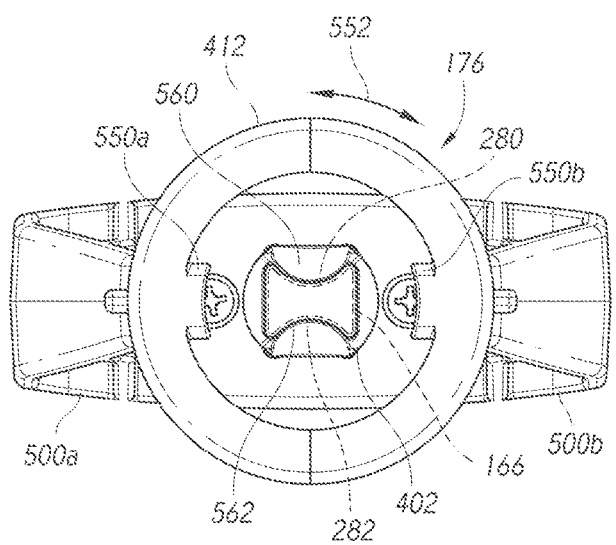
FIG. 23 is a bottom view of the dilation device of FIG. 22.

FIGS. 22 and 23 are side and bottom views, respectively, of the dilator device 176. Referring to FIG. 22, the handle 400 can include handle portions 500a, 500b, a guide 530, and an access opening or window 502 between the handle portions 500a, 500b. The guide 530 can include an opening 532 (FIGS. 17 and 24) positioned generally along the longitudinal axis 541 of the dilator device 176. Other types of handle assemblies can also be used. For example, T-shaped handles or spherical shaped handles can be used, if needed or desired.

Figure 24:
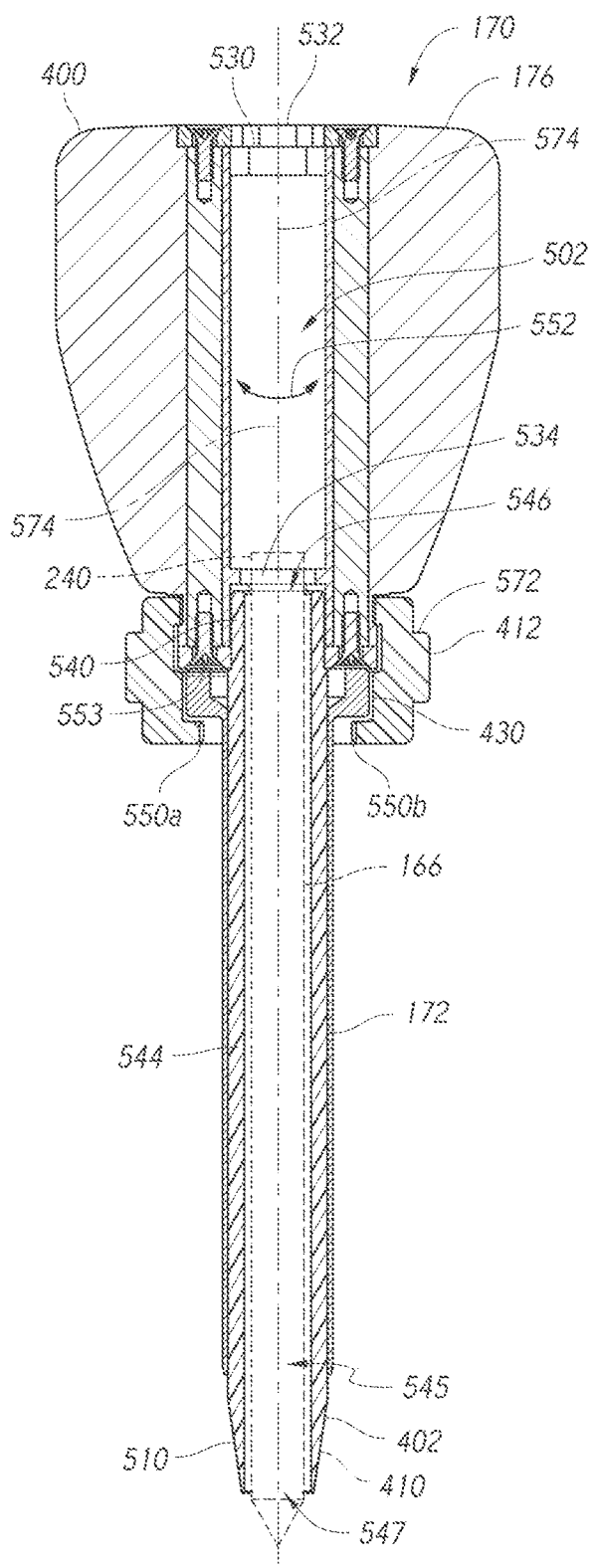
FIG. 24 is a longitudinal cross-sectional view of the cannula dilation assembly of FIGS. 17 and 18 with a locking mechanism in a locked configuration.
Figure 25:
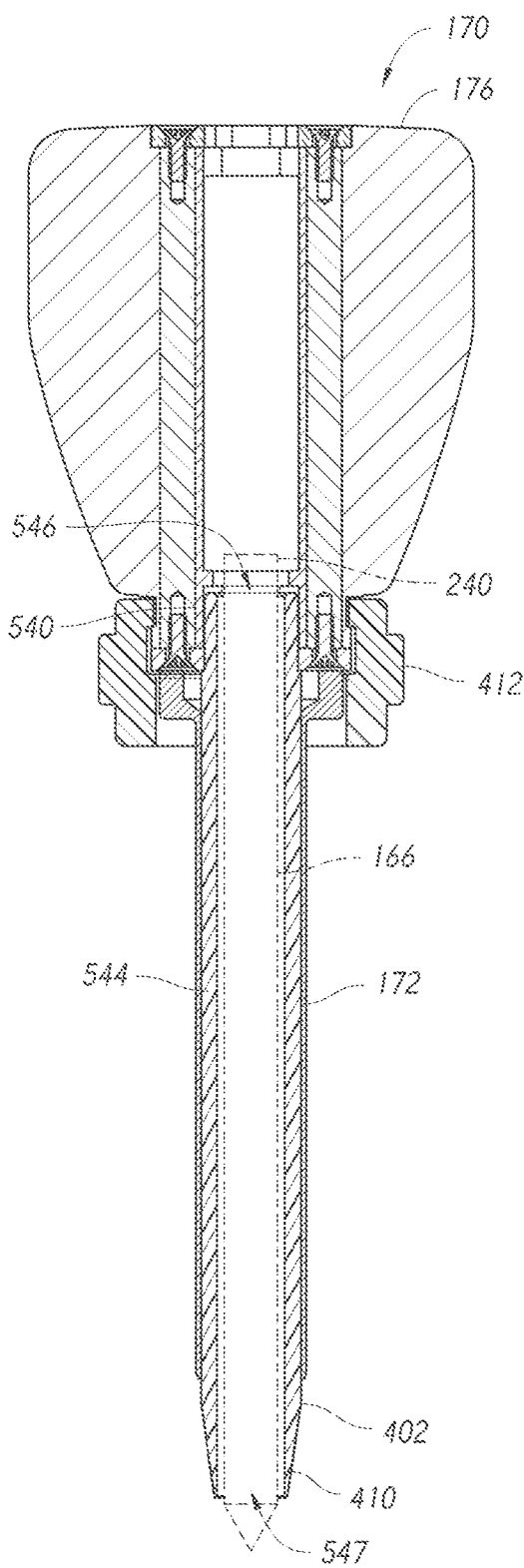
FIG. 25 is a longitudinal cross-sectional view of the cannula dilation assembly with the locking mechanism in an unlocked configuration.

FIGS. 24 and 25 are cross-sectional views of the dilator device 176 holding the introducer dilator 166 (shown in phantom line). The elongate dilator 402 can include the distal end 410, a proximal end 540, and an elongate body 544 therebetween. A passageway 545 extends between openings 546, 547. FIG. 24 shows the locking mechanism 412 in a locked configuration for coupling together the instrument cannula 172 and outer dilation assembly 170. The head 430 of the instrument cannula 172 can be held between retaining features 550a, 550b of the locking mechanism 412 and an abutment 553 of the handle 400. A main body 572 of the locking mechanism 412 can be rotated about an axis of rotation 574 (indicated by arrows 552) until the retaining features 550a, 550b are aligned with the keying features (e.g., keying features 450a, 450b of FIGS. 19A-19B of the head 430). FIG. 25 shows the locking mechanism 412 in the unlocked configuration to align the retaining features 550a, 550b with the keying features 450a, 450b, respectively. As such, the instrument cannula 172 is free to slide distally along the elongate dilator 402 away from the locking mechanism 412.

Figure 26:
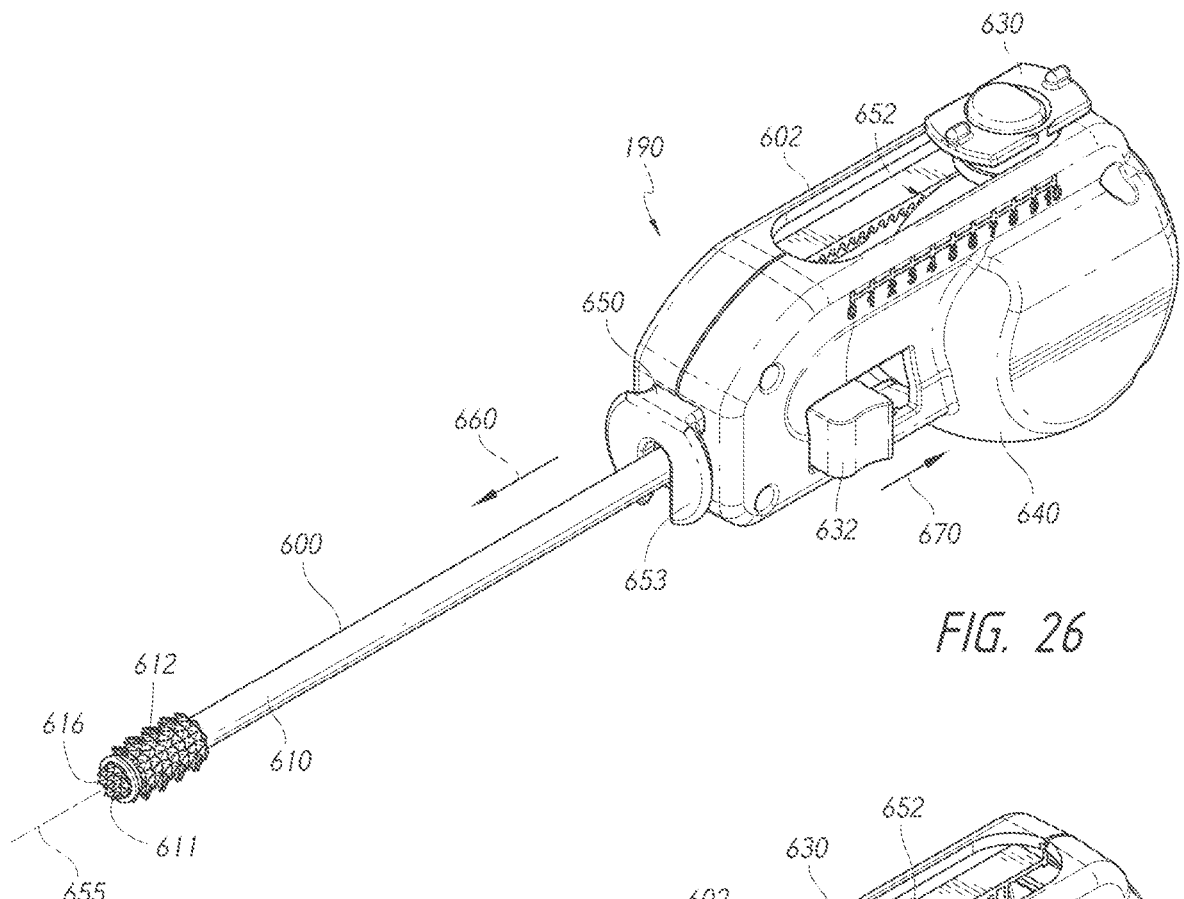
FIG. 26 is an isometric view of a reamer instrument in accordance with an embodiment of the disclosure.
Figure 27:
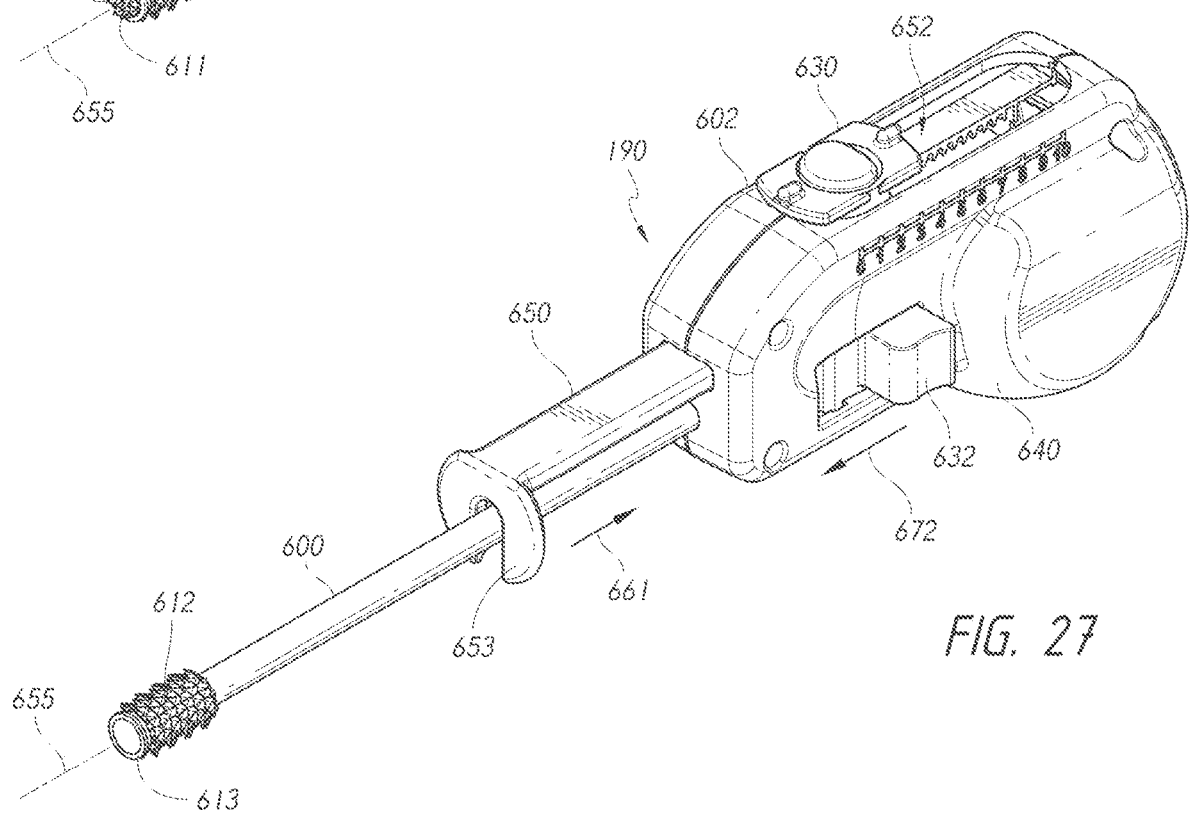
FIG. 27 is an isometric view of the reamer instrument of FIG. 26 with a retracted reaming tip and an extended depth stop member.

FIG. 26 is an isometric view of a reamer instrument 190 in accordance with an embodiment of the disclosure. FIG. 27 is an isometric view of the reamer instrument 190 with a retracted reaming tip and an extended depth stop member 650. Referring now to FIG. 26, the reamer instrument 190 can include a reaming assembly 600 for abrading, scraping, or otherwise mechanically altering bone or tissue and a handle assembly 602 for operating the reaming assembly 600. The reaming assembly 600 can include a reaming tip 611 for contacting distal tissue and a lateral reaming element 612 for contacting lateral tissue. The reaming tips 611, 612 can include a roughened surface, array of sharp protrusions, texturing, or other features capable of loosening, separating, cutting, scraping, or otherwise affecting tissue. For example, the reaming tip 611 can be used to bore through tissue, and the lateral reaming element 612 can be used to ream laterally adjacent tissue. When the tip reaming tip 611 is retracted to an atraumatic position (FIG. 27), it can be positioned inside of the lateral reaming element 612. As shown in FIG. 27, an atraumatic edge 613 can be configured to inhibit or prevent injury to distal tissue. Accordingly, the reaming assembly 600 can be moved between different configurations to target specific tissue during a procedure.

The handle assembly 602 can include, without limitation, a depth stop mechanism 630, a reaming control element 632 ("control element 632"), and a handle housing 640 for protecting internal components. The depth stop mechanism 630 can include the stop member 650 and a positioning assembly 652. The stop member 650 can include a head 653 oriented generally perpendicular to a longitudinal axis 655 of the reaming assembly 600. The positioning assembly 652 can be used to move the stop member 650 distally (indicated by arrow 660 in FIG. 26) or proximally (indicated by arrow 661 in FIG. 27) to adjust, for example, a maximum depth of penetration of the reaming assembly 600. Once the stop member 650 is at the desired location, the positioning assembly 652 can be locked to hold the head 653 stationary relative to the reaming assembly 600. The reaming control element 632 can be moved proximally (indicated by arrow 670 in FIG. 26) to move the reaming tip 611 (FIG. 26) into the lateral reaming element 612. Referring now to FIG. 27, the reaming control element 632 can be moved distally (indicated by arrow 672) to move the reaming tip 611 out of the lateral reaming element 612.

Figure 28:
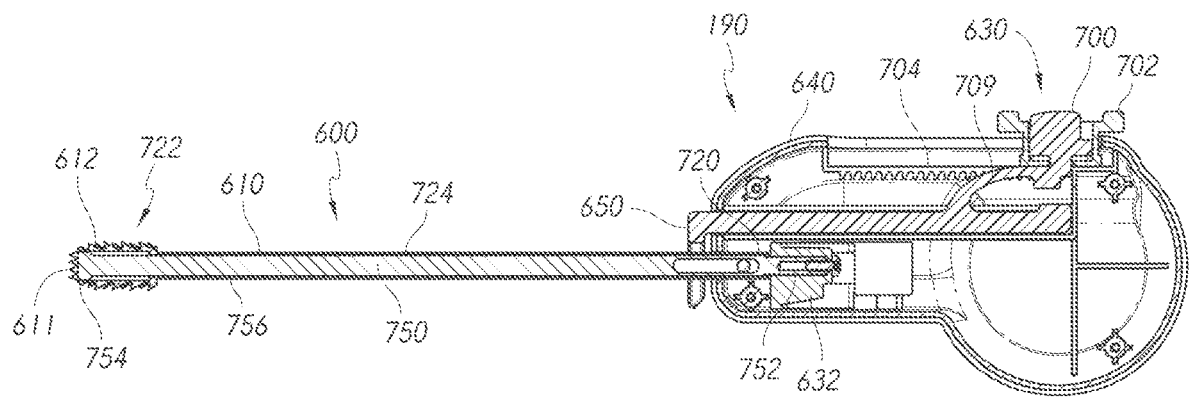
FIG. 28 is a longitudinal cross-sectional view of the reamer instrument of FIG. 26.

FIG. 28 is a longitudinal cross-sectional view of the reamer instrument 190. In one embodiment, the reaming assembly 600 can include an outer reamer member 610 with the lateral reaming element 612 and an inner reamer member 750 with the reaming tip 611. The outer reamer member 610 can have a proximal end 720, a distal end 722, and a hollow elongate main body 724. The proximal end 720 can be fixedly coupled to the handle housing 640. The main body 724 can be a shaft (e.g., a tubular shaft made of metal, plastic, etc.) with an inner surface 740 (FIG. 29) that closely surrounds the inner reamer member 750. The inner reamer member 750 can include a proximal end 752, a distal end 754, and an elongate body 756 (e.g., a solid or hollow rod or shaft made of metal, plastic, etc.). The proximal end 752 can be connected to the control element 632 by, for example, one or more fasteners, pins, welds, or other connection elements. In other embodiments, the proximal end 752 and a control element 632 can have a one-piece construction.

Figure 29:
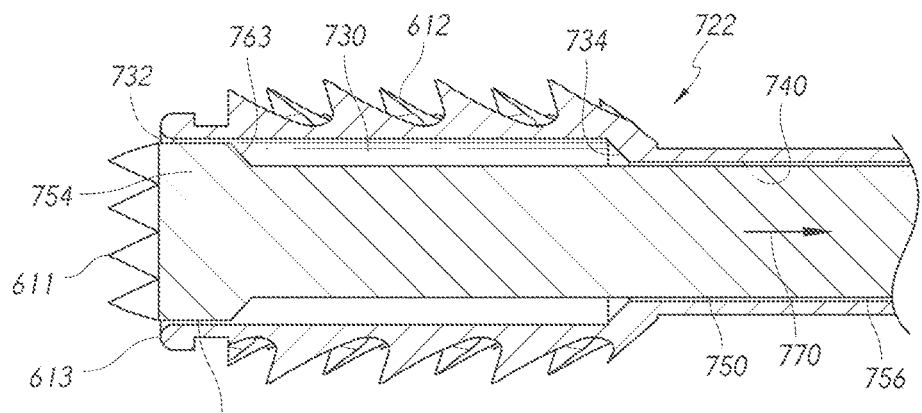
FIG. 29 is a detailed cross-sectional view of a distal portion of the reamer instrument with a reaming tip in a deployed position.
Figure 30:
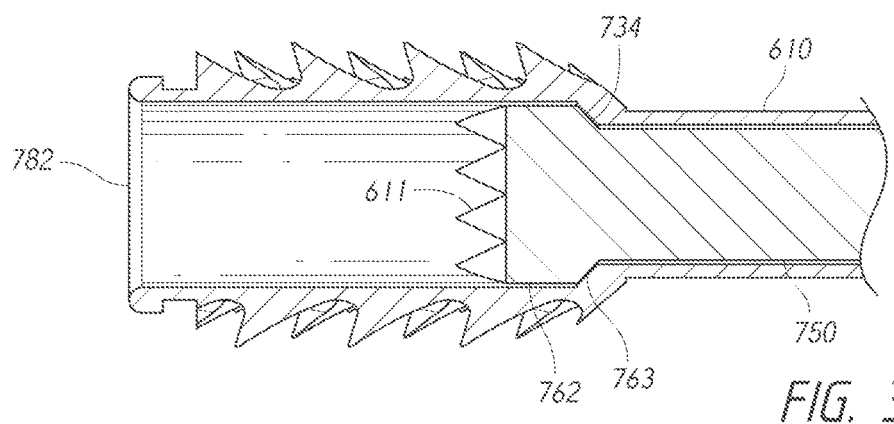
FIG. 30 is a detailed cross-sectional view of the distal portion of the reamer instrument with the reaming tip in a retracted atraumatic position.

FIGS. 29 and 30 are detailed cross-sectional views of the distal end of the reaming assembly 600 in two different configurations. Referring now to FIG. 29, the distal end 722 of the outer reamer member 610 can include an opening 732 and a stop in the form of a shoulder 734. A widened passageway 730 extends from the opening 732 to the shoulder 734. The distal end 754 of the inner reamer member 750 can include a shoulder 763 and a head 762. FIG. 29 shows the reaming tip 611 in a distal reaming position such that the reaming tip 611 protrudes outwardly (distally) from the edge 613 of the distal end 722. The inner reamer member 750 can be moved proximally (indicated by arrow 770 in FIG. 29) until the shoulder 763 contacts the shoulder 734 (FIG. 30).

Referring again to FIG. 7, the deployed reaming tip 611 can be used to abrade tissue (not shown) located posterior to the illustrated ligamentum flavum 615. The reaming assembly can be advanced distally to abrade tissue adjacent to the ligamentum flavum 615 or the tissue of the ligamentum flavum 615. The reaming tip 611 can be retracted to the atraumatic position (FIGS. 27 and 30) to avoid damaging non-targeted tissue, such as the spinal cord 617, which is located between the ligamentum flavum 615 and a ligament 184. The spinal cord 617 extends from the brain to the bottom of the spine and extends through vertebral foramina. Spinal nerves branch from the spinal cord 617 and exit the spine and extend to other parts of the body. The reaming tip 611 can be retracted to avoid traumatizing or damaging nerve tissue, or other non-targeted tissue, such as the epidural sac. With the reaming tip 611, the reamer instrument 190 can be inserted deeper into the subject without risk of tearing or damaging the epidural sac or injuring the spinal cord 617. For example, the atraumatic edge 782 (FIG. 30) can be blunted, rounded, and/or smooth to inhibit, limit, or substantially prevent damage and/or injury to the epidural sac.

Referring again to FIG. 28, the depth stop mechanism 630 can include a control element 700, a slider locking element 702, and a rack 704. The control element 700 can include a cantilevered lever 709 movable between a first position (e.g. an undepressed position, an extended position, etc.) to a second position (e.g., a depressed position, an unextended position, etc.). When the control element 700 is depressed, an engagement feature (e.g., a U-shaped member) can be moved away from teeth of the rack 704. To move the positioning assembly 630 from a locked configuration (FIG. 28) to an unlocked configuration, a user can press down on the control element 700 to overcome a biasing force provided by the element 709 and thereby move the control element 700 downwardly. After the control element 700 is depressed, it can be moved proximally or distally. After the stop member 650 is moved to the desired position, the control element 700 can be released to allow the control element 700 to move back to the undepressed position. Other types of positioning assemblies can be used and can include, without limitation, one or more biasing devices (e.g. springs, actuators, etc.), control elements, gears, or the like. The configuration and functionality of the positioning assemblies can be selected based on the desired operation of the reamer instrument 190.

FIGS. 31-35 illustrate a method of performing at least a portion of a decompression procedure on a patient in accordance with an embodiment of disclosure. Generally, an incision can be made along the patient's back using, for example, a scalpel 780. The introducer dilation assembly 100 can be moved through the incision and inserted between the spinous processes 160, 164. The needle device 167 can be removed from the introducer dilator 166. The dilation assembly 170 can be advanced over the introducer dilator 166 and into the subject. The introducer dilator 166 can then be removed from the dilation assembly 170, and the dilator device 176 can then be removed from the instrument cannula 172. Details of the procedure are discussed below.

FIG. 31 shows the scalpel 780 ready to make an incision along the midline of the subject. An entry point can be selected on the patient's skin to obtain access to the targeted surgical site, and an incision of appropriate length is made through the dermal layers of a patient's body at the entry point. The length and depth of the incision may be larger depending on whether the clinician is using an open, mini-open, or minimally invasive, percutaneous approach. In some procedures, a targeted surgical level can be identified and a midline incision (e.g., 5 mm to 15 mm length incision) can be made under direct visualization, fluoroscopic guidance, or other suitable visualization technique. In some procedures, the supraspinous ligament 150 can be dissected (e.g., longitudinally dissected) to provide access to an interspinous space 174. The scalpel 780, or other cutting instruments, can form incisions at other locations to access the spine using non-midline approaches, such as lateral approaches.

FIG. 32 shows the introducer dilation assembly 100 after it has been passed through the incision and moved through the supraspinous ligament 150. As the introducer dilation assembly 100 is advanced distally, the sharp tip 202 and distal end 204 dilates tissue (e.g., spreads or separates tissue) and/or otherwise affect tissue to facilitate penetration into the patient. As the introducer dilation assembly 100 is initially inserted between the spinous processes 160, 164, it can drive apart the spinous processes. The distracted spinous processes 160, 164 can be positioned in and slide along the channels 280, 282, respectively, (FIG. 12) until the distal end 204 is at the desired depth. The spinous processes 160, 164 in the channels 280, 282, respectively, can inhibit or limit rotation of the introducer dilator 166. Such placement of the introducer dilation assembly 100 with respect to the spinous processes 160, 164 therefore stabilizes the introducer dilation assembly 100.

The introducer dilation assembly 100 can be monitored using fluoroscopy, direct visualization, or other visualization technique. After the introducer dilation assembly 100 is at the desired location, the locking mechanism 212 can be moved from the locked configuration to the unlocked configuration and the needle device 167 can then be pulled out of the introducer dilator 166.

FIG. 33 shows the needle device 167 separated from the introducer dilator 166. A longitudinal axis 781 of the introducer dilator 166 can be generally perpendicular to the patient's spine or at another suitable orientation. For example, the longitudinal axis 781 can be generally parallel to the anterior-to-posterior direction.

Figure 34:
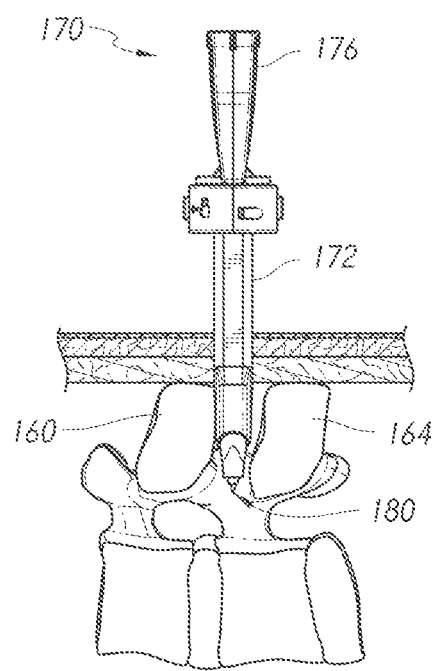

Referring to FIG. 34, the dilation assembly 170 has been inserted over the introducer dilator 166. The dilation assembly 170 can be aligned (e.g., rotationally aligned) with the proximal end 240 of the introducer dilator 166 and then slid over the proximal end 240. As shown in FIG. 23, the alignment features 560, 562 (e.g., convex features) of the elongate dilator 402 can be received by the channels 280, 282 of the introducer dilator 166 to rotationally lock the dilator 402 and the introducer dilator 166. As the dilator 402 moves along the introducer dilator 166, the tapered distal end (FIG. 17) can dilate the incision, spread or separate tissue, and/or otherwise affect tissue to facilitate penetration into the patient. If the spinous processes 160, 164 are sufficiently close together, the distal end 410 can contact and push apart the spinous processes 160, 164.

As the dilation assembly 170 is advanced over the introducer dilator 166, the channels 280, 282 (FIG. 12) of the introducer dilator 166 can be aligned with the respective alignment features 560, 562 (FIG. 23). The spinous processes and/or tissue can move from the channels 280, 282 of the dilator 166 to the respective alignment features 560, 562 of the dilator 402 as the dilation assembly 170 is advanced along the stationary dilator 166. Referring to FIGS. 21 and 34, the channels 480 of the cannula 172 (FIG. 21) can be generally aligned with the channels 442 (FIG. 17) of the elongate dilator 402 such that the spinous processes and/or tissue move from the channels 442 of the dilator 402 to the respective channels 480 of the cannula 172.

Figure 35:
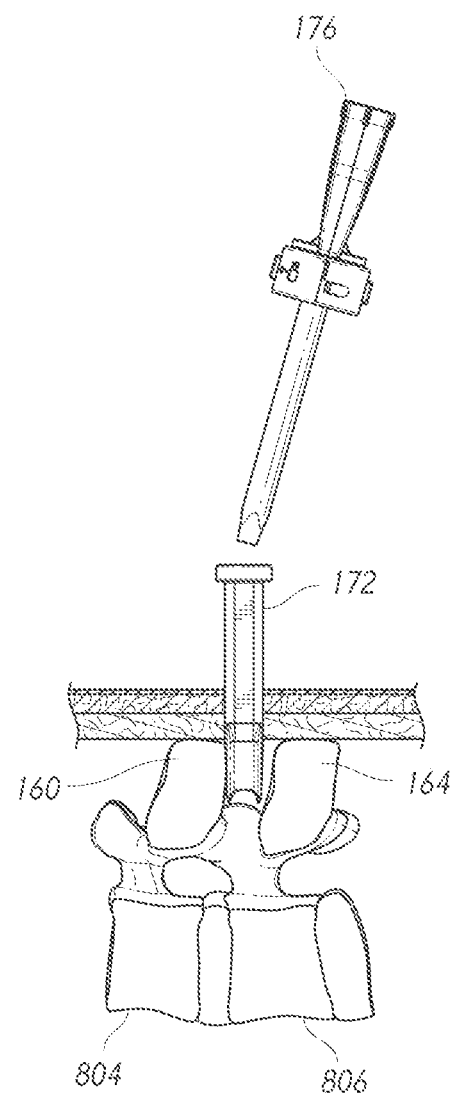
Figure 36:
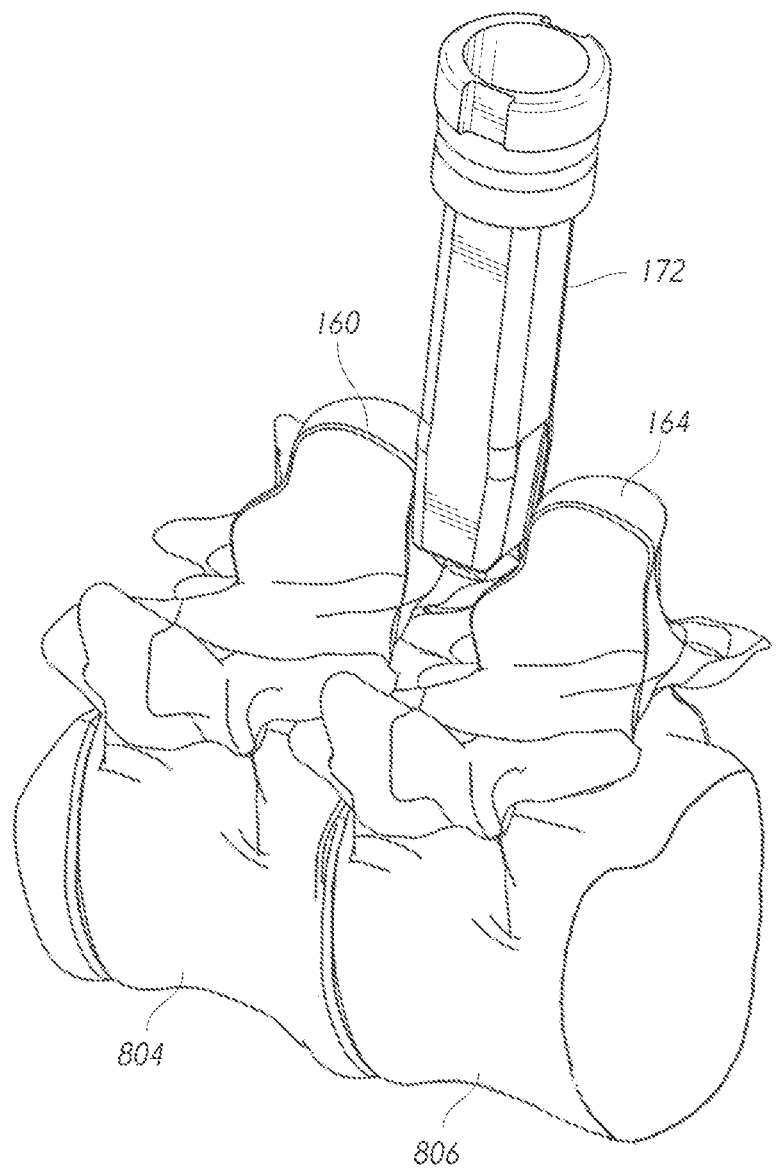
FIG. 36 is an isometric view of an instrument cannula positioned along a spine in accordance with an embodiment of the disclosure.

FIG. 35 shows the dilator device 176 spaced apart from the instrument cannula 172. FIG. 36 shows an instrument cannula 172 positioned between the spinous processes 160, 164. Tips of the spinous processes 160, 164 can be received by the receiving features 460 (see, e.g., FIG. 19A) to set the cannula 172. Any number of different instruments can be delivered through the instrument cannula 172 to treat a wide range of symptoms, conditions, and/or diseases, including, without limitation, spinal nerve compression (e.g., spinal cord compression, spinal nerve root compression, or the like), spinal disk herniation, osteoporosis, stenosis, or other diseases or conditions. In some procedures, the cannula 172 provides access for surgical instruments for performing a spinal cord decompression procedure that includes, without limitation, delivering visualization media, removing bone from one or both vertebrae 804, 806, separating the ligamentum flavum from one or both vertebrae 804, 806, cutting or debulking the ligamentum flavum, and removing loose tissue. A wide range of decompression procedures can be performed and can include, without limitation, a discectomy, osteophyte removal, laminotomy, or other type of decompression procedures for removing bone and/or soft tissue. Each stage of the decompression procedure can be performed with a different instrument or series of instruments.

Instruments can be advanced through the cannula 172 to remove tissue (e.g., bone, connective tissue, etc.) to, for example, reduce spinal compression, increase access to the treatment site, and can be viewed under fluoroscopy or other suitable visualization technique. The cannula 172 can be sufficiently large to allow repositioning of the instruments to access different treatment sites, such as the lateral recesses, facets, ligamentum flavum, or the like. In some simultaneous bilateral access procedures, the cannula 172 can be repositioned while remaining in the patient to remove tissue from opposing lateral recesses or other lateral treatment sites. Additionally, the cannula 172 can provide direct visualization. For example, a user can view the treatment site and/or instrument by looking through the passageway of the cannula 172. Additionally or alternatively, visualization devices (e.g., fiber optics, cameras, light sources, or the like) can be coupled to or incorporated into the cannula 172. After removing the desired amount of bone (or other tissue), the instrument can be withdrawn from the subject.

Fluoroscopy (e.g., anterior-posterior imaging, lateral imaging, contralateral-oblique imaging, etc.) can be used to view the treatment site, tools, and delivery path. In certain procedures, visualization techniques can be used to identify margins of the epidural space, dura, ligamentum flavum, and/or nerve roots relative to the lamina and interlaminar space, as well as the features of instruments. Contrast media can be refreshed to maintain desired imaging. When reaming instruments (e.g., reaming instrument 190) are near nerve tissue, the reaming instruments can be in an atraumatic configuration.

Figure 37:
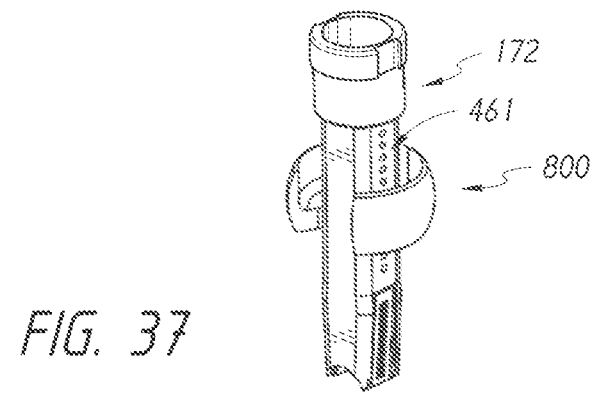
FIGS. 37-39 illustrate a method of assembling an instrument positioner assembly in accordance with an embodiment of the disclosure.
Figure 38:
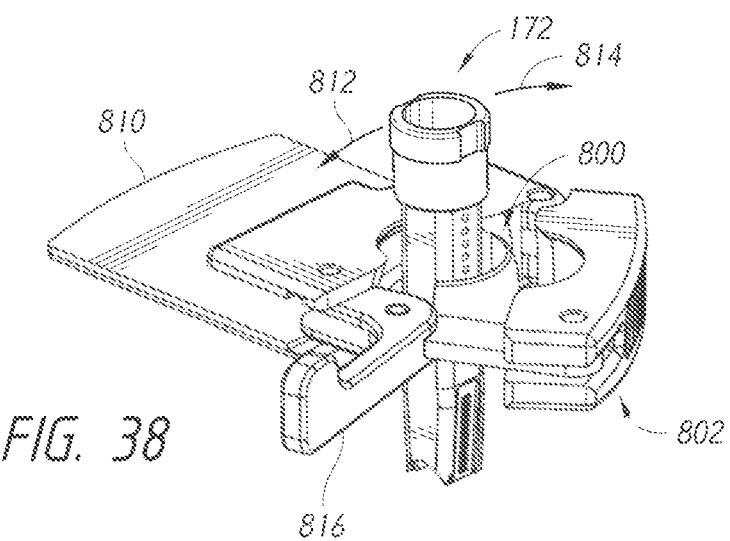
Figure 39:
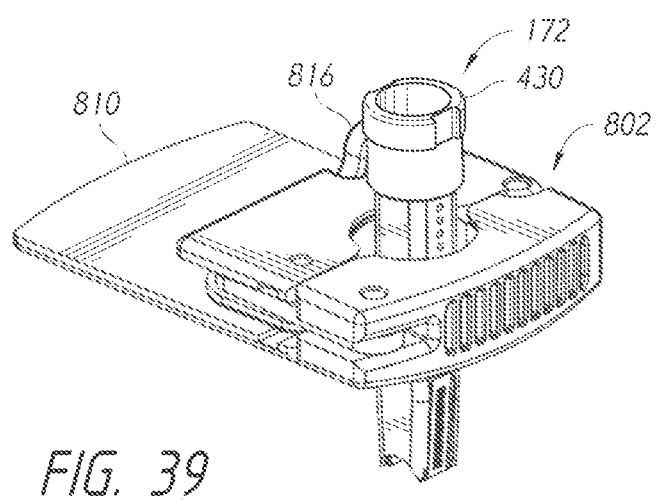

FIGS. 37-39 illustrate a method of assembling a holder in the form of an instrument positioner assembly for holding an instrument cannula in accordance with an embodiment of the disclosure. Generally, the cannula 172 can be installed in a collar 800 positionable in an open clamp assembly 802. The cannula 172 can be rotated relative to the clamp assembly 802. After the cannula 172 is at the desired orientation, the clamp assembly 802 can be closed to securely hold the collar 800. Instruments can be delivered through the cannula 172 while the clamp assembly 802 holds the cannula 172 at the desired orientation. The clamp assembly 802 can be opened to reorient the cannula 172. Non-limiting exemplary methods of using the clamp assembly 802 are discussed below.

A user can select a desired axial position along the cannula 172 for the collar 800 based on, for example, the distance from the patient's skin to the treatment site. FIG. 37 shows the collar 800 coupled to the cannula 172 and ready for installation in the clamp assembly 802. The collar 800 can include protrusions or other features matable with one or more locators 461 of the cannula 172. The illustrated cannula 172 includes an array of spaced apart locators 461 that can be, for example, recess, holes, or the like. The cannula 172 can be inserted into the patient before or after installing the collar 800.

The clamp assembly 802 can be placed over the collar 800. A base 810 (FIG. 38) can rest against the patient's skin and can extend in the superior direction (or other direction). The cannula 172 can be rotated in the lateral direction (indicated by arrows 812, 814) or other desired direction. The base 810 can inhibit or limit rocking movement of the clamp assembly 802 (e.g., rocking in the superior direction), thereby stabilizing the cannula 172.

Referring to FIG. 38, a lever mechanism 816 can be used to close and open the clamp assembly 802. FIG. 39 shows the closed clamp assembly 802 with the rotationally fixed collar 800. The cannula 172 can be keyed to the collar 800 to prevent axial movement of the cannula 172, and the clamp assembly 802 can be opened to adjust the orientation of the cannula 172. When an instrument is positioned in the cannula 172, a depth stop mechanism of the instrument can contact the cannula 172 to limit movement of the instrument in the distal direction. By way of example, the stop member 650 discussed in connection with FIGS. 26-27 can contact the proximal end (e.g., head 430) of the cannula 172 and thereby limit the penetration depth of the reamer instrument 190. By adjusting the position of the stop member 650 (FIGS. 26-27), the penetration depth of the reamer instrument 190 can be adjusted to safely access targeted tissue.

Figure 40:
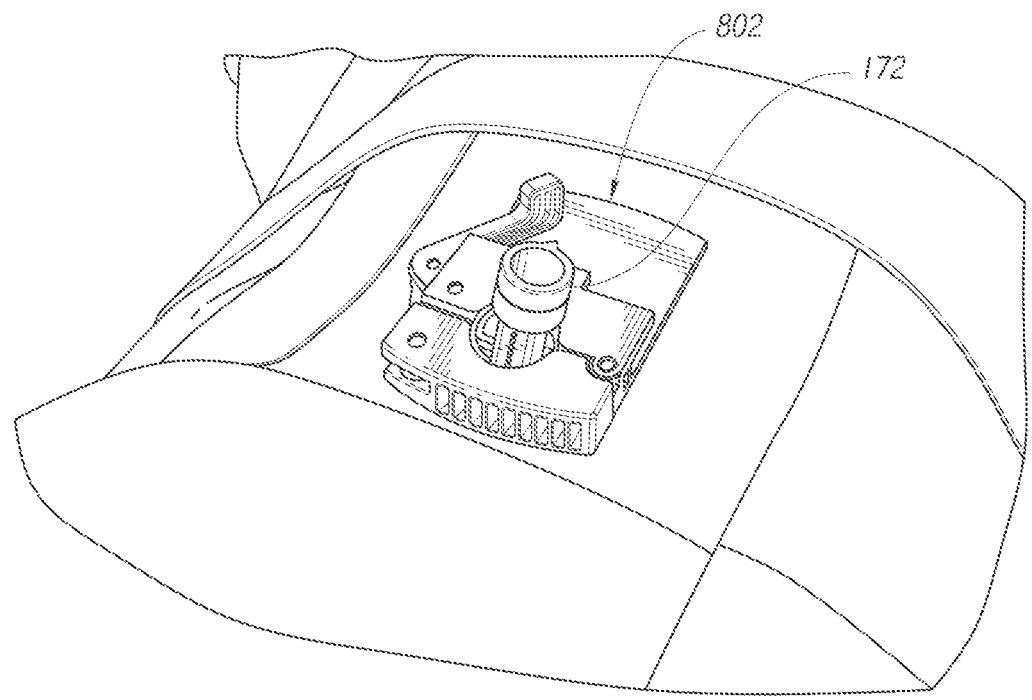
FIGS. 40-42 illustrate an instrument positioner assembly holding an instrument cannula in a patient.
Figure 41:
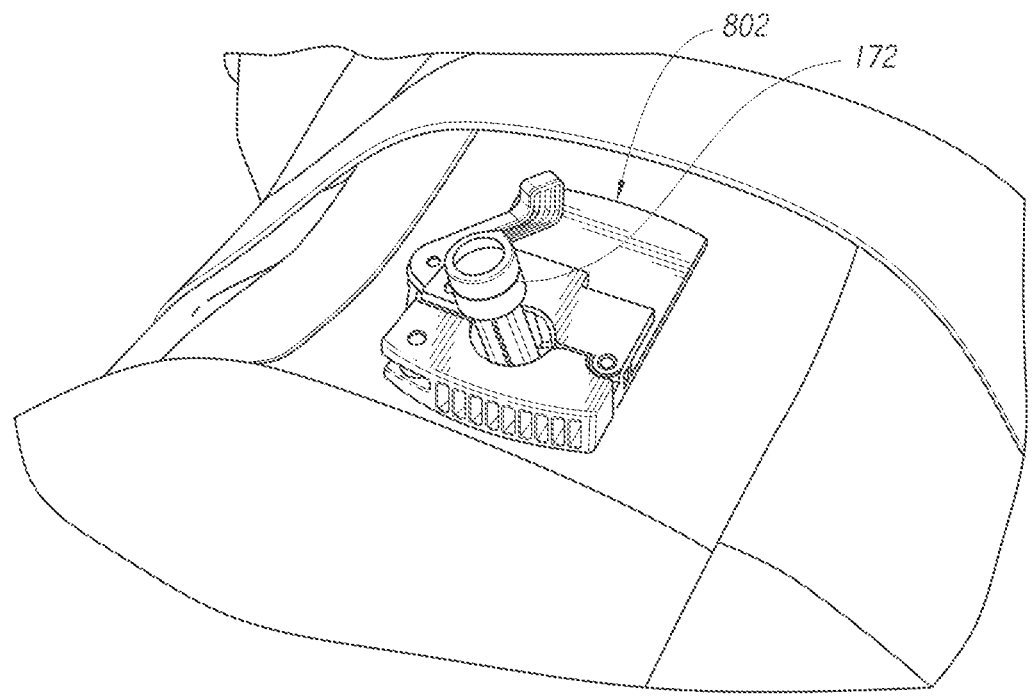
Figure 42:
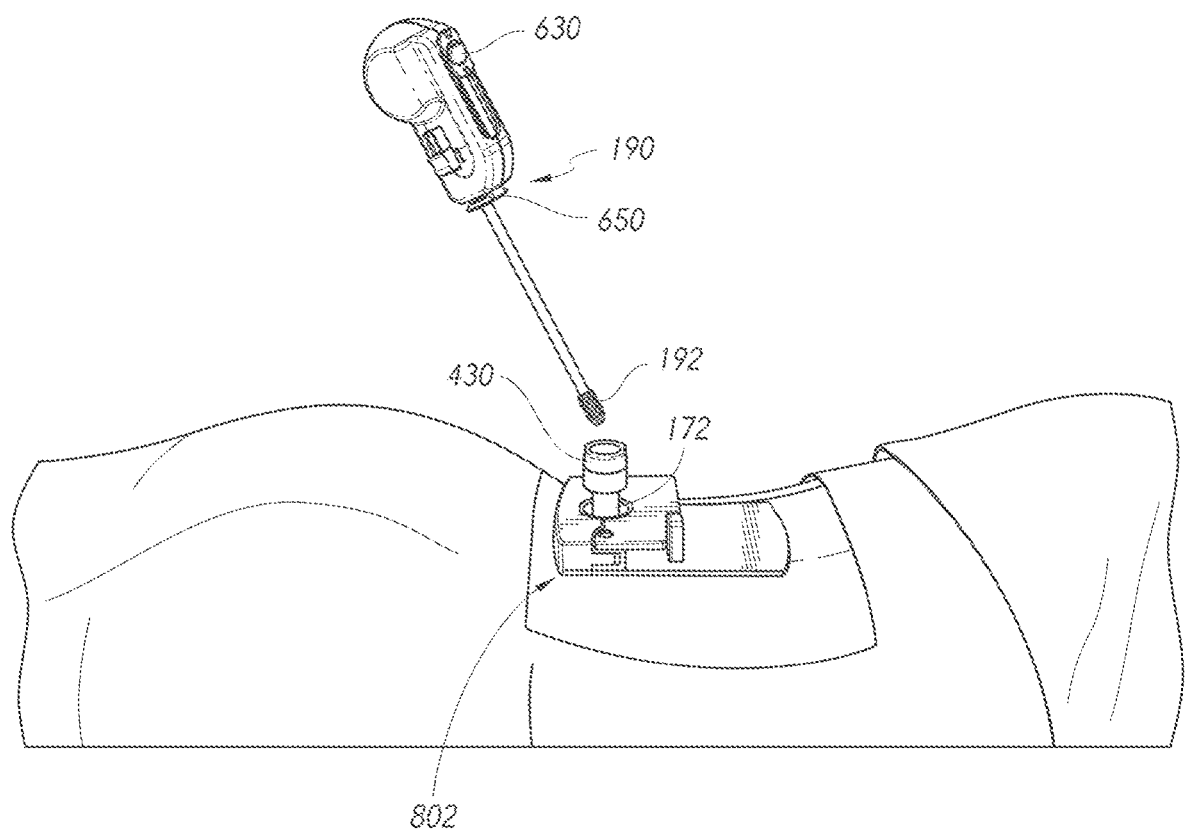

FIGS. 40-42 illustrate the clamp assembly 802 positioned on a patient. The cannula 172 of FIG. 40 is positioned to access left regions of the subject's left lateral vertebrae recess of a vertebral body. The cannula 172 of FIG. 41 is positioned to access the right regions of the subject's right lateral recess of the vertebral body. FIG. 42 shows the reamer instrument 190 ready to be delivered through the cannula 172. Visualization techniques can be used to confirm the position, trajectory, and depth of the end of instrument cannula 172, instrument(s), etc. The dimensions (e.g., diameter) of the passageway 470 (FIG. 19B) of the cannula 172 can be sufficiently large to allow repositioning of the instrument to access different treatment sites, such as the lateral recesses, facets, ligamentum flavum, or the like. In some simultaneous bilateral access procedures, the cannula 172 can be repositioned while remaining in the patient to remove tissue from opposing lateral recesses or other lateral treatment sites. Additionally, the cannula 172 can provide direct visualization. For example, a user can view the treatment site and/or instrument by looking through the passageway 470 (FIG. 19B). Additionally or alternatively, visualization devices (e.g., fiber optics, cameras, or the like) can be coupled to or incorporated into the cannula 172 and/or instruments for viewing.

In some procedures, the reamer instrument 190 can extend a distance (e.g., 10 mm, 15 mm, 20 mm, etc.) past the distal end of the cannula 172 when the stop member 650 contacts the head 430. The reamer instrument 190 can be rotated to abrade, loosen, tear, or otherwise alter tissue and can be removed any number of times to remove residual tissue (e.g., ligament tissue, bone tissue, etc.) attached to the reamer instrument. Different types of instruments can be used to cut bone, create one or more defects (e.g., a generally hemispherical defect) in the inferior medial aspect of the superior lamina, or otherwise prepare the treatment site.

To remove midline tissue, the cannula 172 can be oriented towards the midline interlaminar region. A reamer instrument can be inserted through the cannula 172 and positioned towards the midline position of the superior lamina. In one exemplary embodiment, the depth stop mechanism 630 of the reamer instrument 190 can be used to, for example, prevent injury to the dural or other non-targeted tissue. Visualization techniques can be used to monitor the position on the reamer head. In some procedures, the reamer head can be moved from midline to left lateral or the right lateral. Any number of reamer instruments can be used to remove the desired amount of midline lamina bone. The depth stop mechanism can be used to allow access to the targeted region while maintaining a desired distance from the epidural space and other vital structures. After performing the reaming procedure, the reamer can be removed from the patient and a preparation procedure can be performed. The preparation procedure can include, without limitation, irrigating the treatment site, removing residual tissue (e.g., via suction), applying one or more agents (e.g., hemostatic agents), or other procedures.

A debulker instrument can be used to provide a complete blunt dissection of the ligamentum flavum from the lamina and disrupt ligamentous tissue. In some procedures, the debulker instrument is inserted through the cannulas and positioned at a midline position of the superior lamina. The depth stop mechanisms can facilitate positioning of the distal tip (e.g., debulking head) at the most dorsal margin of the superior lamina. Intraoperative fluoroscopy and/or tactile feedback can be used to confirm positioning. While maintaining a midline trajectory, the distal tip of the debulker instrument can be gently moved around the inferior lamina lip and repositioned against the bony underside. The adjustable depth stop can be reset, if desired, to allow access to the targeted region while maintaining a desired distance from the epidural space and other vital structures. The properly positioned distal tip can engage the underside of the lamina and resist attempts to gently withdraw the instrument.

The debulking tip can dissect and separate the ligamentum flavum from the lamina when it is move from midline toward the lateral recess. A subtle left-right sweeping motion can be used disrupt ligamentous tissue and help extend the desired tissue plane. The distal tip can be moved until it reaches the most lateral desired position. The depth stop mechanism can be adjusted to allow access to the lateral recesses. The debulker tip can be moved slightly inferior and out from the lamina underside. The debulker tip can be used to continually debulk the ligamentum flavum. The depth stop mechanism can be adjusted to allow access to the targeted region, while intraoperative fluoroscopy is used to verify the distal tip position and maintain a safe working distance from the epidural space and/or other vital structures. After performing the debulking procedure, the debulker instrument can be removed from the patient and a preparation procedure can be performed.

The lamina can be removed using a tissue removal instrument. The cannula 172 can be oriented towards the desired interlaminar region (e.g., left or right interlaminar region). A closed jaw assembly of a tissue removal instrument can be moved through the cannula 172 towards a generally midline position. A depth stop mechanism can be used to adjust the depth of penetration until the jaw assembly is positioned proximate the most dorsal margin of the superior lamina. The jaw assembly can be closed to remove tissue. While maintaining midline trajectory, the jaw assembly can be moved around the inferior lamina lip and positioned against the bony underside. The depth stop can be adjusted to allow access to the targeted region while maintaining a desired distance from the epidural space and other vital structures. The distal or lower jaw of the jaw assembly can engage the underside of the lamina and the proximal or upper jaw can be positioned just dorsal to the lamina. The jaw assembly can be held against the targeted lamina bone while the jaw assembly is closed. The tissue removal instrument can be withdrawn from the patient. The jaw assembly can be opened to release the captured material. This process can be repeated to remove bone and other tissue in the lateral direction until the desired decompression is achieved.

Systems, components, and instruments disclosed herein can be disposable or reusable. For example, the reamer instrument 190 can be disposable to prevent cross-contamination. As used herein, the term "disposable" when applied to a system or component (or combination of components), such as an instrument, a tool, or a distal tip or a head (e.g., a reamer head, a jaw assembly, etc.), is a broad term and generally means, without limitation, that the system or component in question is used a finite number of times and is then discarded. Some disposable components are used only once and are then discarded. In other embodiments, the components and instruments are non-disposable and can be used any number of times.

Figure 43:
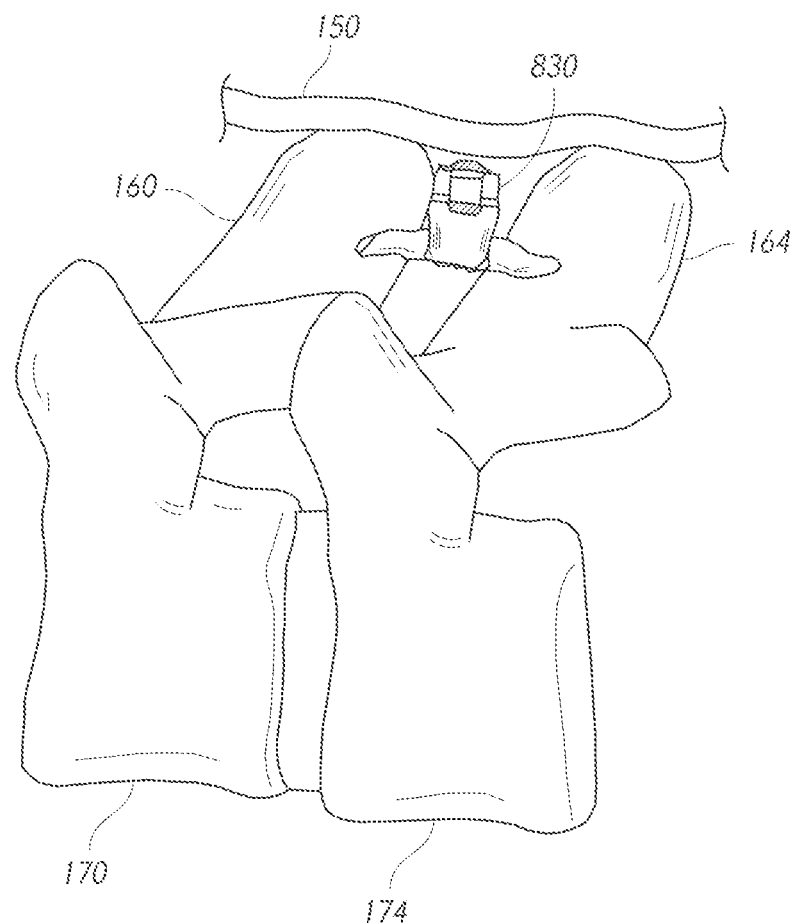
FIG. 43 is a side view of a device implanted in a patient in accordance with an embodiment of the disclosure.

The cannula 172 can be used deliver one or more spinal implants before, after, or during tissue removal. The methods of delivery, delivery instruments, dilators, spinal implants, and other features of U.S. Pat. Nos. 8,012,207; 8,123,807; 8,152,837; U.S. application Ser. No. 12/217,662 (corresponding U.S. Pub. No. 20080287997); U.S. application Ser. No. 13/844,173; U.S. application Ser. No. 12/358,010, and U.S. application Ser. No. 13/844,324. U.S. Pat. Nos. 8,012,207; 8,123,807; 8,152,837; U.S. application Ser. No. 12/217,662 (corresponding U.S. Pub. No. 20080287997); U.S. application Ser. No. 13/844,173; U.S. application Ser. No. 12/358,010, and U.S. application Ser. No. 13/844,324 are hereby incorporated by reference in their entireties. FIG. 43 shows an implanted device 830 positioned between the spinous processes 160, 164. The device 830 can be delivered via the cannula or other access device. In one embodiment, the device 830 is a SUPERION® Interspinous Spacer from VertiFlex, Inc. (San Clemente, CA) or a similar device. The device 830 can be implanted while imaging using visualization media and/or direct visualization.

C. Visualization Systems and Procedures

Visualization can be used throughout an entire decompression procedures or stage(s) of decompression procedures. Visualization systems and components disclosed herein can be incorporated into or used with dilation systems, introducer dilation assemblies, cannula dilation assemblies, instrument cannulas, dilation devices, instrument positioner assemblies, reamer instruments, and other systems and components disclosed herein.

Figure 44:
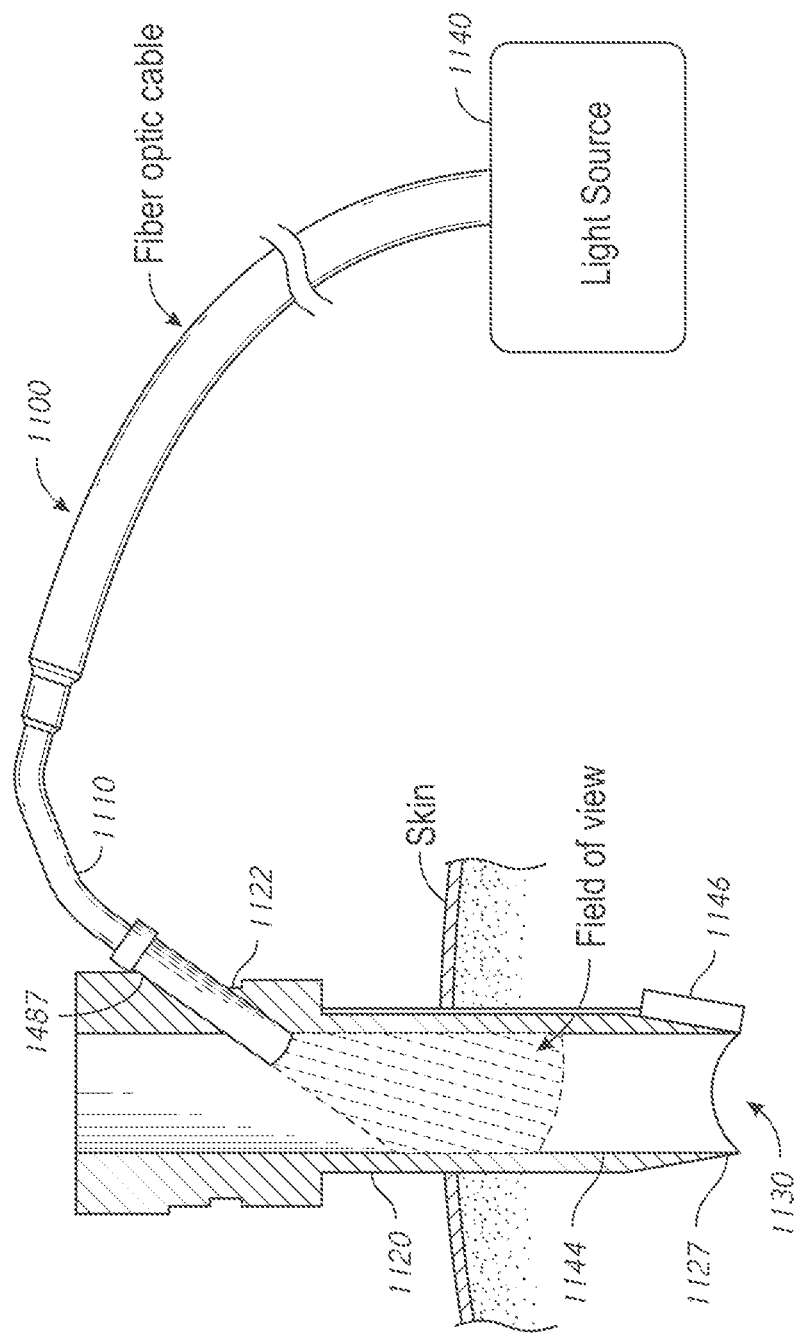
FIG. 44 is a side view of a cannula and a visualization system in accordance with an embodiment of the disclosure.

FIG. 44 is a side view of a visualization system 1100 in accordance with one embodiment of the disclosure. The visualization system 1100 can include an illumination instrument 1110 and an access device in the form of a cannula 1120. The cannula 1120 can be similar or identical to the cannula 172 discussed in connection with FIGS. 21A-21C. The cannula 1120 of FIG. 44 can extend through a subject's skin, subcutaneous tissue, and/or a supraspinal ligament. The illumination instrument 1110 can extend through a sidewall 1122 of the cannula 1120 and can direct light toward a working space 1130. In some embodiments, the instrument 1110 passes through an access features 1487 and can include a light source 1140 and a waveguide. The light source 1140 can output light suitable for viewing tissue with the naked eye or with an optical aid, such as loupes. The waveguide can include a flexible fiber optic cable (illustrated) configured to deliver the light from the light source 1140 towards the space 1130.

An inner surface 1144 of the cannula 1120 can reflect the light to enhance light delivery to the working space 1130. In some embodiments, the inner surface 1144 can include one or more optically reflective coatings. In other embodiments, the cannula 1120 can include one or more reflective elements (e.g., mirrors) for directing light out an open distal end 1127 of the cannula 1120. The cannula 1120 can have one or more imaging devices 1146 positioned to image the working space 1130, and the imaging devices 1146 can include one or more light sources oriented to illuminate tissue within its field of view.

Figure 45:
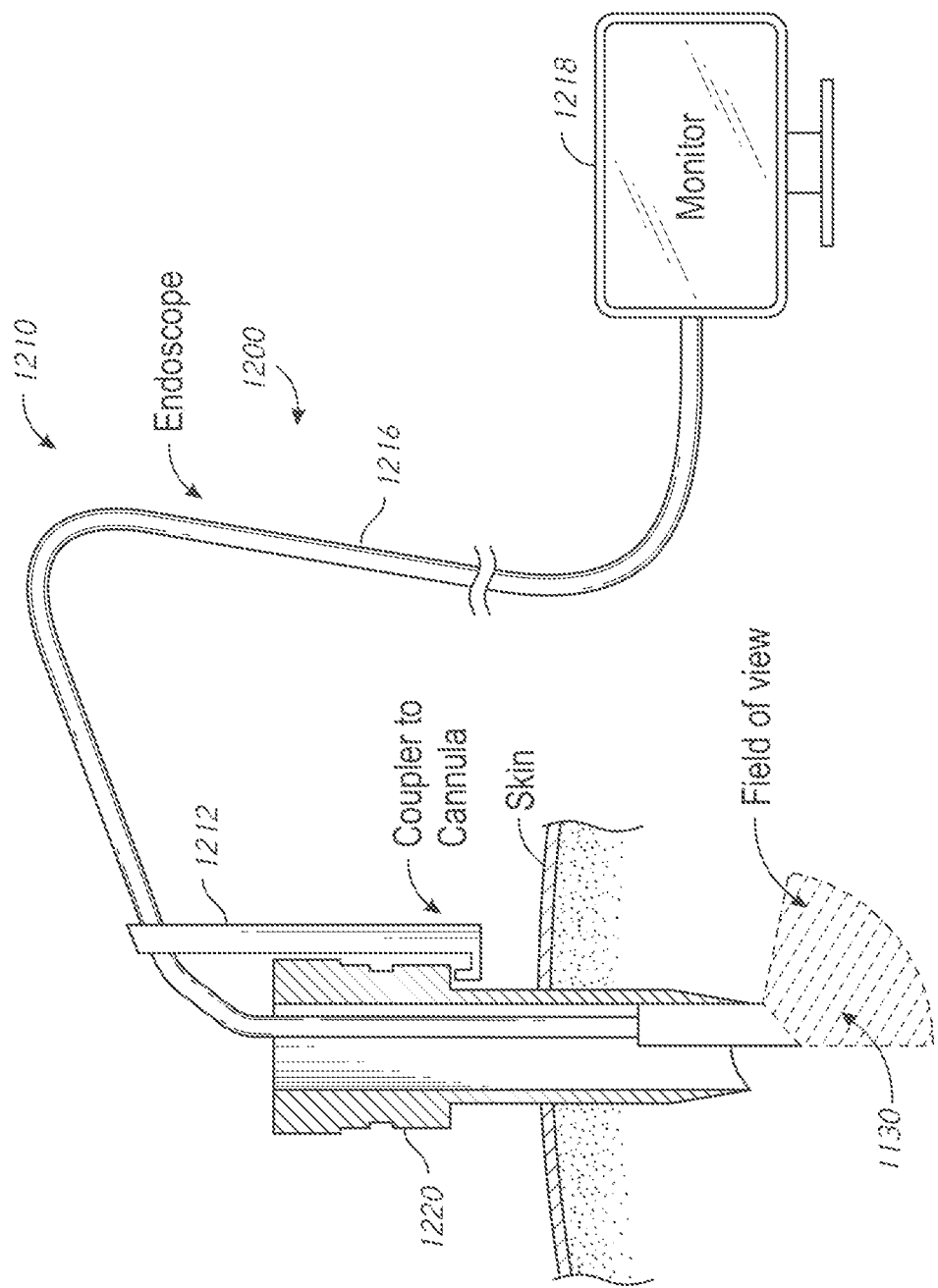
FIG. 45 is a side view of a cannula and a visualization system coupled to the cannula in accordance with an embodiment of the disclosure.

FIG. 45 is a side view of a visualization system 1200 in accordance with one embodiment of the disclosure. The visualization system 1200 can include an imaging instrument 1210 and a cannula 1220. The imaging instrument 1210 is positioned within a lumen of the cannula 1220 and can provide a field of view for viewing the working space 1130 (including regions of the working space 1130 not viewable by direct viewing). The imaging instrument 1210 can be an endoscope or other imaging device for providing a desired field of view. A coupler 1212 can help keep the imaging instrument 1210 positioned to view the working space 1130 while allowing rotation of the imaging instrument 1210 relative to the cannula 1220. In one embodiment, the imaging instrument 1210 can be rotated 360 degrees to provide complete peripheral viewing of tissue not viewable with the naked eye. The orientation of the field of view can be selected based on the desired peripheral viewing. The imaging instrument 1210 can be a visualization instrument with an endoscope 1216 and a viewing device, such as monitor 1218.

Figure 46:
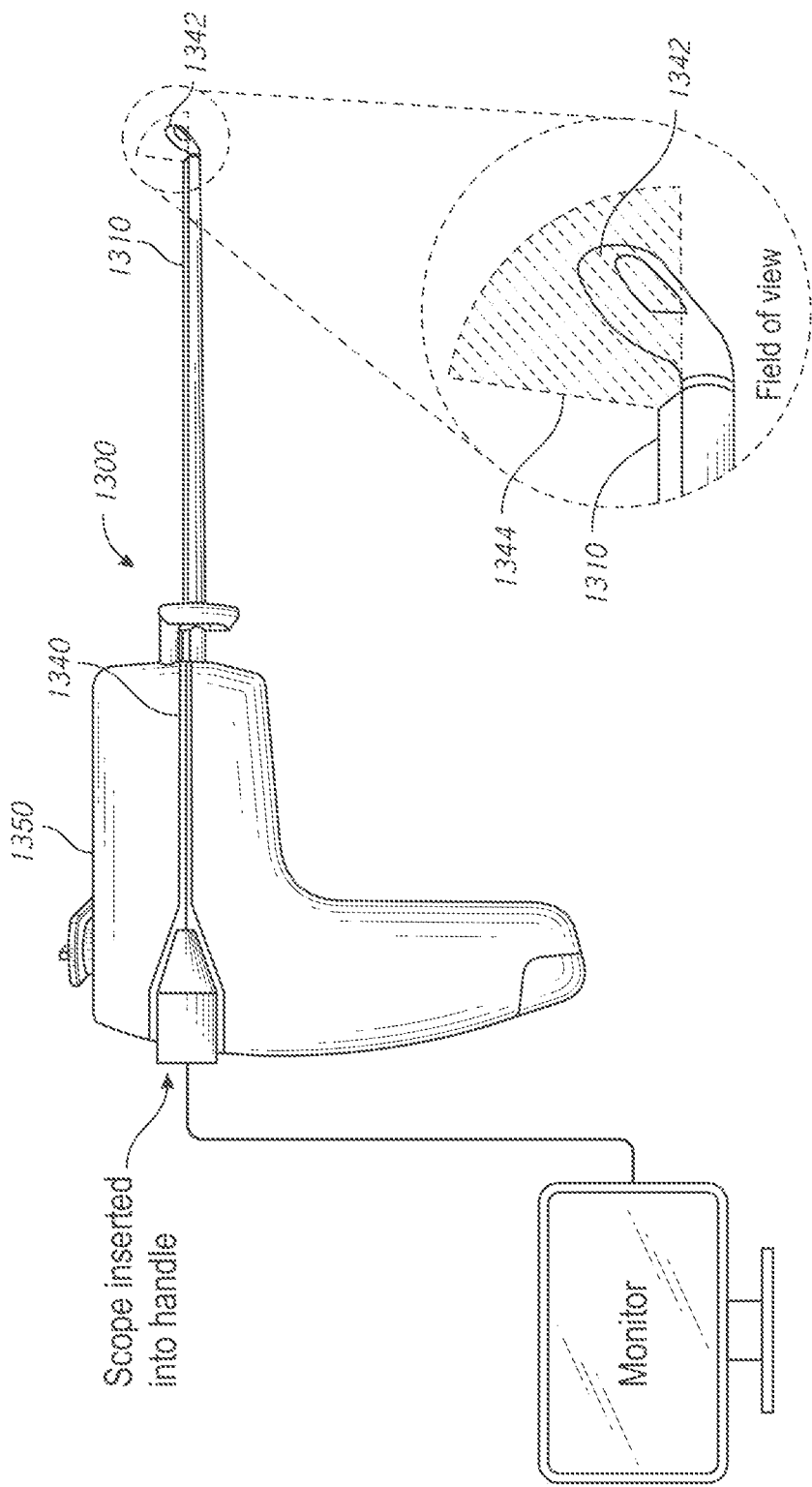
FIG. 46 is a side view of a spinal decompression instrument and a visualization system in accordance with an embodiment of the disclosure.

FIG. 46 is a side view of a visualization system 1300 in accordance with one embodiment of the disclosure. The visualization system 1300 can include a visualization instrument 1310 extending through a lumen 1340 of a decompression instrument 1350. The decompression instrument 1350 can be identical or similar to the decompression instrument 190 of FIGS. 26 and 27. A distal end 1342 shown in FIG. 46 can be positioned in the field of view 1344 of the instrument 1310. In some embodiments, the visualization instrument 1310 can include a monitor and an endoscope connected to the monitor. The configuration of the visualization instrument 1310 can be selected based on the configuration of the decompression instrument 1350.

Figure 47:
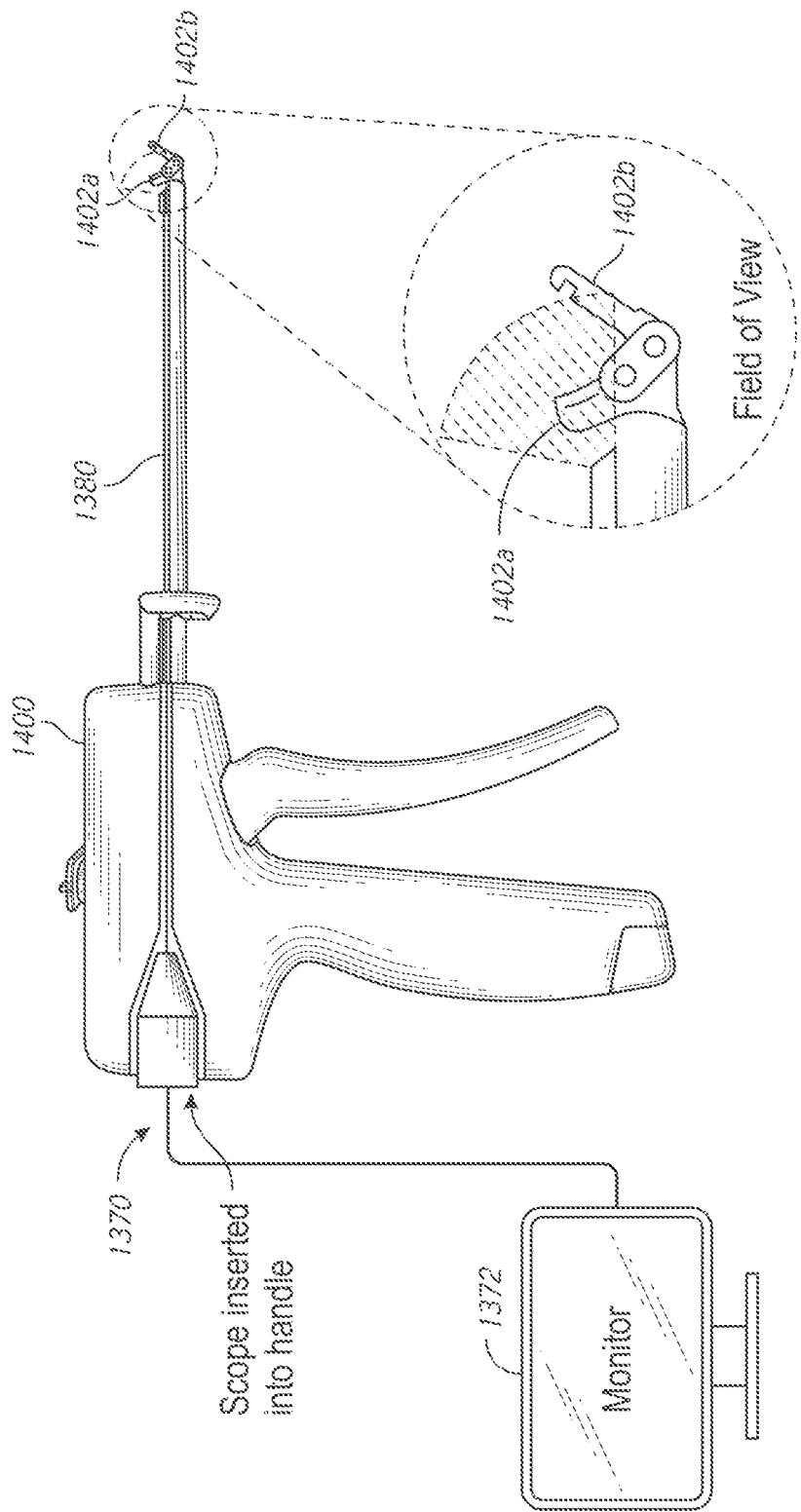
FIG. 47 is a side view of a spinal decompression instrument and a visualization system in accordance with another embodiment of the disclosure.

FIG. 47 is a side view of the visualization system 1370 including a monitor 1372 and a visualization instrument 1380 extending through a decompression instrument in the form of a rongeur 1400. The field of view of the visualization instrument 1380 can include at least a portion of the rongeur 1400 to accurately positioning jaws 1402a, 1402b. The configuration and position of the instrument 1380 can be selected to provide viewing of the tissue grabbed by the jaws 1402a, 1402b.

The visualization systems disclosed herein can be utilized with a wide range of different types of decompression instruments. A spinal procedure can be performed while viewing the treatment to help, for example, remove tissue to perform a decompression procedure and avoid damaging non-targeted tissue. For example, viewing can help perform one or more of the steps discussed in connection with FIGS. 2-7 and 31-43. In some procedures, a spinal procedure can be performed without utilizing additional view, such as fluoroscopic viewing. In some embodiments, visualization systems disclosed herein can be used with fluoroscopic viewing or other imaging techniques. The various embodiments described herein may also be combined to provide further embodiments. For example, features from various instruments can be combined with features and methods disclosed in U.S. Pat. Nos. 8,012,207; 8,123,807; 8,152,837, U.S. application Ser. No. 12/217,662 (U.S. Publication No. 2008/0287997), and U.S. application Ser. No. 13/844,324, which are incorporated by reference in their entireties and a part of the present specification. A wide range of visualization instruments and treatment instruments can be used to address a wide range of symptoms, conditions, and/or diseases, including, without limitation, spinal nerve compression (e.g., spinal cord compression, spinal nerve root compression, or the like), spinal disk herniation, osteoporosis, stenosis, or other diseases or conditions.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. For example, visualization media can be delivered before, during, or after positioning a cannula (e.g., instrument cannula 172 of FIGS. 19-21). Additionally, the instruments (e.g., tissue removal instruments, reamer instruments, debulker instruments, dilators, syringes, etc.) can have one or more stops (e.g., depth stops) to inhibit or prevent injury or damage to tissue. Additionally or alternatively, the stops can be incorporated into the cannulas (e.g., cannulas or instruments disclosed herein). The various embodiments described herein may also be combined to provide further embodiments. For example, features from various instruments can be combined with features disclosed in U.S. Pat. Nos. 8,012,207; 8,123,807; 8,152,837, U.S. application Ser. No. 12/217,662 (U.S. Publication No. 2008/0287997), and U.S. application Ser. No. 12/358,010, which are hereby incorporated by reference herein and made a part of this application.

Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A dilation system for sequentially dilating anatomical features to provide access to a treatment site along a spine of a subject, the dilation system comprising:
    a first dilator having a first end and a second end configured to be inserted between adjacent spinous processes of the subject,
    an instrument cannula having a first cannula end, a second cannula end, and an instrument passageway extending between the first and second cannula ends, and
    a second dilator configured for insertion into the instrument passageway of the instrument cannula via the first cannula end and to extend beyond the second cannula end of the instrument cannula,
    wherein instrument cannula and the second dilator are configured for delivery over the first dilator and insertion of the second cannula end of the instrument cannula between the adjacent spinous processes of the subject, wherein, after insertion of the second cannula end of the instrument cannula between the adjacent spinous processes of the subject, the dilation system is configured for removal of the first dilator and the second dilator from the instrument passageway to permit insertion of an instrument through the instrument passageway.

2. The dilation system of claim 1, further comprising a first handle removably coupleable to the first dilator.

3. The dilation system of claim 2, further comprising a first locking mechanism movable between a locked configuration for coupling together the first dilator and the first handle and an unlocked configuration for allowing the first handle to be decoupled from the first dilator.

4. The dilation system of claim 1, further comprising a second handle coupled to the second dilator.

5. The dilation system of claim 1, wherein the second handle is configured to removably couple to the instrument cannula.

6. The dilation system of claim 5, further comprises a second locking mechanism movable between a locked configuration for coupling together the instrument cannula and the second handle and an unlocked configuration for allowing the second handle to be decoupled from the instrument cannula.

7. The dilation system of claim 1, wherein the second dilator has oppositely located outer channels, and wherein the instrument cannula has oppositely located outer cannula channels alignable with the oppositely located outer channels of the second dilator such that the adjacent spinous processes move from the oppositely located outer channels of the second dilator to the respective oppositely located outer cannula channels as the second cannula end of the instrument cannula is inserted between the adjacent spinous processes.

8. The dilation system of claim 7, wherein the first dilator has oppositely located outer channels.

9. The dilation system of claim 8, wherein the second dilator is configured to be movable over the first dilator only when the oppositely located outer channels of the first dilator are aligned with the oppositely located outer channels of the second dilator.

10. The dilation system of claim 8, wherein the oppositely located outer channels of the first dilator extend from a proximal end portion of the first dilator to a distal end portion of the first dilator.

11. The dilation system of claim 10, wherein the second dilator comprises a channel having an arcuate profile corresponding to a shape of the oppositely located outer channels of the first dilator.

12. A method for accessing a treatment site along a spine of a subject, the method comprising:
inserting the first dilator of the dilation system of claim 1 into the subject such that a portion of the first dilator is positioned between adjacent spinous processes of the subject;
moving the second dilator and instrument cannula over the first dilator;
inserting the instrument canula and the second dilator into the subject so that the second cannula end is positioned between the adjacent spinous processes of the subject;
removing the second dilator from the instrument cannula; and
removing the first dilator from the instrument cannula leaving the second cannula end of the instrument cannula positioned between the adjacent spinous processes of the subject.

13. The method of claim 12, further comprising
prior to inserting the first dilator, coupling a first handle to the first dilator; and
after inserting the first dilator, removing the first handle from the first dilator to permit the moving of the second dilator and instrument cannula over the first dilator.

14. The method of claim 13, wherein the coupling comprises locking the first handle to the first dilator using a first locking mechanism and wherein the removing comprising unlocking the first handle from the first dilator using the first locking mechanism.

15. The method of claim 12, further comprising:
prior to the moving, coupling a second handle to the instrument cannula, wherein the second handle is attached to the second dilator.

16. The method of claim 15, wherein the coupling comprises locking the second handle to the instrument cannula using a second locking mechanism and wherein the removing comprising unlocking the second handle from the instrument cannula using the second locking mechanism.

17. The method of claim 12, further comprising, prior to the moving, inserting the second dilator into the instrument passageway of the instrument cannula.

18. The method of claim 17, wherein the moving comprises aligning oppositely located outer channels of the first dilator with oppositely located outer channels of the second dilator.

19. The method of claim 17, wherein the moving comprises aligning a channel of the second dilator with oppositely located outer channels of the first dilator, the channel having an arcuate profile corresponding to a shape of the oppositely located outer channels of the first dilator.

20. The method of claim 12, further comprising, after removing the second dilator and the first dilator, inserting an instrument into the instrument passageway of the instrument cannula.

* * * * *